United States Patent [19]

Caprathe et al.

[11] Patent Number: 4,762,843

[45] Date of Patent: Aug. 9, 1988

[54] HETERO [F] FUSED CARBOCYCLIC PYRIDINES AS DOPAMINERGIC AGENTS

[75] Inventors: Bradley W. Caprathe, Redford; Juan C. Jaen, Plymouth; Lawrence D. Wise, Ann Arbor, all of Mich.

[73] Assignee: Warner-Lambert Company, Morris Plains, N.J.

[21] Appl. No.: 75,002

[22] Filed: Jul. 17, 1987

Related U.S. Application Data

[63] Continuation-in-part of Ser. No. 907,445, Sep. 15, 1986, abandoned.

[51] Int. Cl.$^4$ ............... A61K 31/345; C07D 498/04; C07D 513/04
[52] U.S. Cl. .................... 514/293; 514/292; 514/267; 546/83; 546/82; 544/250
[58] Field of Search ............ 546/83; 514/292

[56] References Cited

U.S. PATENT DOCUMENTS

| | | | |
|---|---|---|---|
| 4,198,415 | 4/1980 | Kornfeld et al. | 546/83 |
| 4,501,890 | 2/1985 | Nichols et al. | 546/83 |
| 4,537,893 | 8/1985 | Titus et al. | 546/83 |
| 4,552,956 | 11/1985 | Booher et al. | 546/83 |
| 4,596,871 | 6/1986 | Schaus et al. | 546/83 |

FOREIGN PATENT DOCUMENTS 0172697  2/1986  European Pat. Off. ......... 546/83

*Primary Examiner*—Mary C. Lee
*Assistant Examiner*—J. Richter
*Attorney, Agent, or Firm*—Ronald A. Daignault

[57] ABSTRACT

Hetero [f] fused carbocyclic pyridines are described, as well as methods for the preparation and pharmaceutical compositions of same, which are useful as dopamine agonists with selectivity for the presynaptic dopamine receptor and are useful as dopaminergic, antipsychotic and antihypertensive agents as well as for treating hyperprolactinaemia-related conditions and central nervous system disorders.

55 Claims, No Drawings

HETERO [F] FUSED CARBOCYCLIC PYRIDINES AS DOPAMINERGIC AGENTS

This is a continuation-in-part of U.S. application Ser. No. 907,445 filed Sept. 15, 1986 and now abandoned.

BACKGROUND OF THE INVENTION

Compounds of formulas A to E

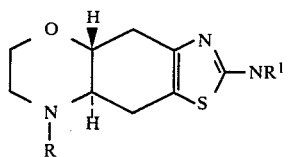

A

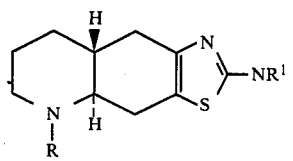

B

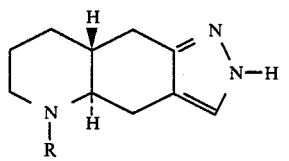

C

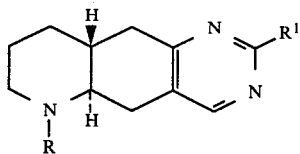

D

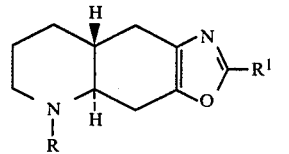

E are described as dopamine agonists in U.S. Pat. Nos. 4,552,956, 4,537,893, 4,198,415, 4,501,890 and European Patent Application No. 172,697 respectively.

Compounds of formula F

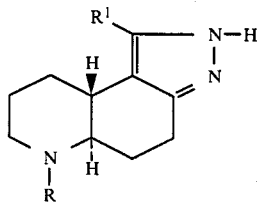

F are described as hypotensive agents in U.S. Pat. No. 4,596,871.

An object of the present invention was to find a dopamine agonist having selectivity for the presynaptic dopamine receptor, i.e. an autoreceptor. The advantage of an autoreceptor agonist is that it modulates the activity of dopaminergic systems selectively, without the postsynaptic stimulation which is inherent to nonselective dopamine agonists.

SUMMARY OF THE INVENTION

Accordingly the present invention is a compound of the formula I

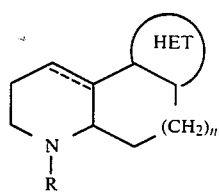

I wherein --- indicates the presence of a single or dobule bond; HET is selected from the group consisting of

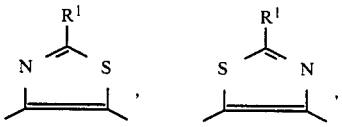

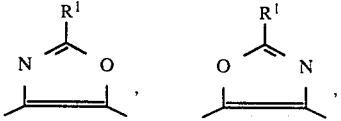

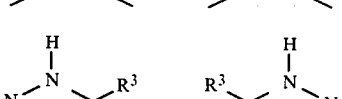

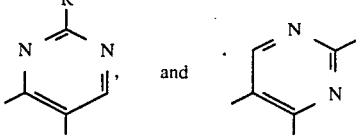

and ;

R is hydrogen, alkyl, alkenyl, cycloalkylalkyl, arylalkyl,

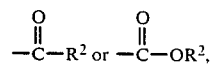

in which $R^2$ is alkyl or arylalkyl; $R^1$ is hydrogen, alkyl or $NR^3R^4$, in which $R^3$ is hydrogen or alkyl and $R^4$ is hydrogen, alkyl, alkenyl, cycloalkylalkyl, arylalkyl,

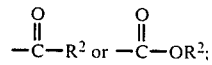

n=0, 1 or 2; and corresponding geometric and optical isomers thereof; or a pharmaceutically acceptable acid addition salt thereof, with the exclusion of a compound of formula

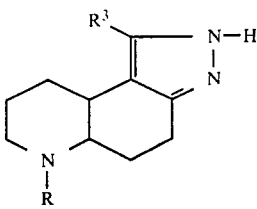

wherein R and $R^3$ are as defined above.

As dopamine agonists with selectivity for the presynaptic dopamine receptor, the compounds of formula I are useful as antipsychotic agents for treating schizophrenia. They are also useful as antihypertensives and for the treatment of disorders which respond to dopaminergic activation. Thus, other embodiments of the present invention include the treatment, by a compound of formula I, of hyperprolactinaemia-related conditions, such as galactorrhea, amenorrhea, menstrual disorders and sexual disfunction, and several central nervous system disorders, such as Parkinson's disease, Huntington's chorea and depression.

A still further embodiment of the present invention is a pharmaceutical composition for administering an effective amount of a compound of formula I in unit dosage form in the treatment methods mentioned above.

Finally, the present invention is directed to methods for production of a compound of formula I.

DETAILED DESCRIPTION OF THE EMBODIMENTS

In the above formula I, when the symbol --- indicates a double bond, the compounds have the formula II

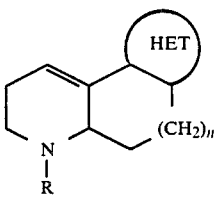

When the symbol --- indicates a single bond, the compounds may exist in a cis- or trans-geometric configuration and can therefore be illustrated by the formulas III or IV

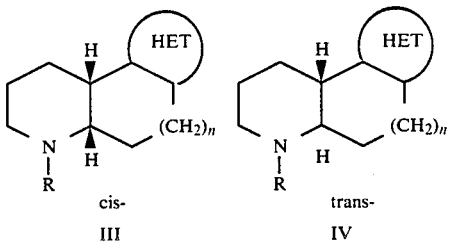

The present invention includes both the cis- and the trans-geometric isomers; the trans-geometric isomers are preferred. Since compounds of formulas II, III and IV possess asymmetric carbon atoms (optical centers), the racemates as well as the individual enantiomers are also included.

In the compounds of formula I, the term "alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl and the like.

The term "alkenyl" means a straight or branched unsaturated hydrocarbon radical having from three to six carbon atoms and includes, for example, allyl, 2-butenyl, 3-methyl-3-butenyl and the like.

The term "cycloalkylalkyl" means a saturated hydrocarbon ring attached to an alkyl group wherein alkyl is as defined above. The saturated hydrocarbon ring contains from three to six carbon atoms. Examples of such are cyclopropylmethyl, cyclohexylmethyl, and the like.

The term "arylalkyl" means an aromatic radical attached to an alkyl radical wherein alkyl is as defined above. The aromatic radical is a phenyl group or phenyl group substituted by one to four substituents selected from alkyl, alkoxy, halogen or trifluoromethyl. Examples of such are benzyl, phenethyl and various substituted benzyl and phenethyl radicals.

"Alkoxy" is O-alkyl in which alkyl is as defined above.

"Halogen" is fluorine, chlorine, bromine or iodine.

Pharmaceutically acceptable acid addition salts of the compounds of formula I include salts derived from non-toxic inorganic acids, such as hydrochloric, nitric, phosphoric, sulfuric, hydrobromic, hydriodic, phosphorous and the like, as well as the salts derived from non-toxic organic acids, such as aliphatic mono and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate.

A preferred compound of formula I is one wherein R is hydrogen, alkyl, alkenyl, cyclopropylmethyl,

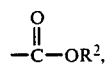

benzyl or phenylethyl and $R^1$ is hydrogen or $NR^3R^4$ which $R^3$ is hydrogen or alkyl and $R^4$ is hydrogen, alkyl, benzyl,

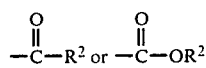

in which $R^2$ is alkyl or arylalkyl.

Another preferred embodiment is a compound of formula I wherein R is hydrogen, methyl, ethyl, allyl, n-propyl, n-butyl, cyclopropylmethyl,

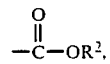

benzyl or phenylethyl and $R^1$ is hydrogen or $NR^3R^4$ in which $R^3$ is hydrogen or alkyl and $R^4$ is hydrogen, methyl, ethyl, n-propyl,

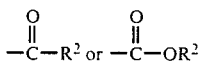

in which R² is alkyl or arylalkyl.

Still another preferred embodiment is a compound of formula I wherein R is hydrogen, methyl, ethyl, allyl, n-propyl, n-butyl, cyclopropylmethyl, benzyl or phenylethyl and R¹ is hydrogen or NR³R⁴ in which R³ is hydrogen and R⁴ is hydrogen,

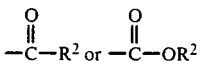

in which R² is alkyl or arylalkyl.

Particularly valuable are:
(±) 4,5,5a,6,7,8-hexahydro-6-propylthiazolo[4,5-f]quinolin-2-amine;
(±) cis-4,5,5a,6,7,8,9,9a-octahydrothiazolo[4,5-f]quinolin-2-amine;
(±) trans-4,5,5a,6,7,8,9,9a-octahydrothiazolo[4,5-f]quinolin-2-amine;
(±) cis-4,5,5a,6,7,8,9,9a-octahydro-6-propylthiazolo[4,5-f]quinolin-2-amine;
(±) trans-4,5,5a,6,7,8,9,9a-octahydro-6-propylthiazolo[4,5-f]quinolin-2-amine;
(+) 4,5,5a,6,7,8-hexahydro-6-propylthiazolo[4,5-f]quinolin-2-amine;
(−) 4,5,5a,6,7,8-hexahydro-6-propylthiazolo[4,5-f]quinolin-2-amine;
(±) 4,5,5a,6,7,8-hexahydrothiazolo[4,5-f]quinolin-2-amine;
(+) 4,5,5a,6,7,8-hexahydrothiazolo[4,5-f]quinolin-2-amine;
(−) 4,5,5a,6,7,8-hexahydrothiazolo[4,5-f]quinolin-2-amine;
(±) 4,5,5a,6,7,8-hexahydro-6-methylthiazolo[4,5-f]quinolin-2-amine;
(+) 4,5,5a,6,7,8-hexahydro-6-methylthiazolo[4,5-f]quinolin-2-amine;
(−) 4,5,5a,6,7,8-hexahydro-6-methylthiazolo[4,5-f]quinolin-2-amine;
(±) 6-ethyl-4,5,5a,6,7,8-hexahydrothiazolo[4,5-f]quinolin-2-amine;
(+) 6-ethyl-4,5,5a,6,7,8-hexahydrothiazolo[4,5-f]quinolin-2-amine;
(−) 6-ethyl-4,5,5a,6,7,8-hexahydrothiazolo[4,5-f]quinolin-2-amine;
(±) 6-butyl-4,5,5a,6,7,8-hexahydrothiazolo[4,5-f]quinolin-2-amine;
(+) 6-butyl-4,5,5a,6,7,8-hexahydrothiazolo[4,5-f]quinolin-2-amine;
(−) 6-butyl-4,5,5a,6,7,8-hexahydrothiazolo[4,5-f]quinolin-2-amine;
(±) 4,5,5a,6,7,8-hexahydro-6-(2-propenyl)thiazolo [4,5-f]quinolin-2-amine;
(+) 4,5,5a,6,7,8-hexahydro-6-(2-propenyl)thiazolo [4,5-f]quinolin-2-amine;
(−) 4,5,5a,6,7,8-hexahydro-6-(2-propenyl)thiazolo [4,5-f]quinolin-2-amine;
(±) 6-(cyclopropylmethyl)-4,5,5a,6,7,8-hexahydrothiazolo[4,5-f]quinolin-2-amine;
(+) 6-(cyclopropylmethyl)-4,5,5a,6,7,8-hexahydrothiazolo[4,5-f]quinolin-2-amine;
(−) 6-(cyclopropylmethyl)-4,5,5a,6,7,8-hexahydrothiazolo[4,5-f]quinolin-2-amine;
(±) 4,5,5a,6,7,8-hexahydro-6-(2-phenylethyl)thiazolo[4,5-f]quinolin-2-amine;
(+) 4,5,5a,6,7,8-hexahydro-6-(2-phenylethyl)thiazolo[4,5-f]quinolin-2-amine;
(−) 4,5,5a,6,7,8-hexahydro-6-(2-phenylethyl)thiazolo[4,5-f]quinolin-2-amine;
(±) 4,5,5a,6,7,8-hexahydro-6-(phenylmethyl)thiazolo[4,5-f]quinolin-2-amine;
(+) 4,5,5a,6,7,8-hexahydro-6-(phenylmethyl)thiazolo[4,5-f]quinolin-2-amine;
(−) 4,5,5a,6,7,8-hexahydro-6-(phenylmethyl)thiazolo[4,5-f]quinolin-2-amine;
(±) N-(4,5,5a,6,7,8-hexahydro-6-methylthiazolo[4,5-f]quinolin-2-yl)-2-methylpropanamide;
(+) N-(4,5,5a,6,7,8-hexahydro-6-methylthiazolo [4,5-f]quinolin-2-yl)-2-methylpropanamide;
(−) N-(4,5,5a,6,7,8-hexahydro-6-methylthiazolo [4,5-f]quinolin-2-yl)-2-methylpropanamide;
(±) N-(4,5,5a,6,7,8-hexahydro-6-propylthiazolo[4,5-f]quinolin-2-yl)acetamide;
(+) N-(4,5,5a,6,7,8-hexahydro-6-propylthiazolo [4,5-f]quinolin-2-yl)acetamide;
(−) N-(4,5,5a,6,7,8-hexahydro-6-propylthiazolo [4,5-f]quinolin-2-yl)acetamide;
(±) N-[4,5,5a,6,7,8-hexahydro-6-(2-propenyl)thiazolo[4,5-f]quinolin-2-yl]acetamide;
(+) N-[4,5,5a,6,7,8-hexahydro-6-(2-propenyl)thiazolo[4,5-f]quinolin-2-yl]acetamide;
(−) N-[4,5,5a,6,7,8-hexahydro-6-(2-propenyl)thiazolo[4,5-f]quinolin-2-yl]acetamide;
(±) N-(4,5,5a,6,7,8-hexahydro-6-propylthiazolo[4,5-f]quinolin-2-yl)-2-methylpropanamide;
(+) N-(4,5,5a,6,7,8-hexahydro-6-propylthiazolo [4,5-f]quinolin-2-yl)-2-methylpropanamide;
(−) N-(4,5,5a,6,7,8-hexahydro-6-propylthiazolo [4,5-f]quinolin-2-yl)-2-methylpropanamide;
(±) trans-4,5,5a,6,7,8,9,9a-octahydro-6-propylthiazolo[5,4-f]quinolin-2-amine;
(±) 4,5,5a,6,7,8-hexahydro-6-propylthiazolo[5,4-f]quinolin-2-amine;
(+) 4,5,5a,6,7,8-hexahydro-6-propylthiazolo[5,4-f]quinolin-2-amine;
(−) 4,5,5a,6,7,8-hexahydro-6-propylthiazolo[5,4-f]quinolin-2-amine;
(±) trans-5,6,6a,7,8,9,10,10a-octahydro-7-propylpyrido[2,3-h]quinazolin-2-amine;
(±) 5,6,6a,7,8,9-hexahydro-7-methylpyrido[2,3-h]quinazolin-2-amine;
(+) 5,6,6a,7,8,9-hexahydro-7-methylpyrido[2,3-h]quinazolin-2-amine;
(−) 5,6,6a,7,8,9-hexahydro-7-methylpyrido[2,3-h]quinazolin-2-amine;
(±) 5,6,6a,7,8,9-hexahydro-7-propylpyrido[2,3-h]quinazolin-2-amine;
(+) 5,6,6a,7,8,9-hexahydro-7-propylpyrido[2,3-h]quinazolin-2-amine;
(−) 5,6,6a,7,8,9-hexahydro-7-propylpyrido[2,3-h]quinazolin-2-amine;
(±) 5,6,6a,7,8,9-hexahydro-7-(2-propenyl)-pyrido [2,3-h]quinazolin-2-amine;
(+) 5,6,6a,7,8,9-hexahydro-7-(2-propenyl)-pyrido [2,3-h]quinazolin-2-amine;
(−) 5,6,6a,7,8,9-hexahydro-7-(2-propenyl)-pyrido [2,3-h]quinazolin-2-amine;
(±) 5,6,6a,7,8,9-hexahydro-7-propylpyrido[3,2-f]quinazolin-3-amine;
(+) 5,6,6a,7,8,9-hexahydro-7-propylpyrido[3,2-f]quinazolin-3-amine;

(−) 5,6,6a,7,8,9-hexahydro-7-propylpyrido[3,2-f]quinazolin-3-amine;

(±) trans-5,6,6a,7,8,9,10,10a-octahydro-7-propyl-pyrido[3,2-f]quinazolin-3-amine;

(±) 4,5,5a,6,7,8-hexahydro-6-propyloxazolo[5,4-f]quinolin-2-amine;

(+) 4,5,5a,6,7,8-hexahydro-6-propyloxazolo[5,4-f]quinolin-2-amine;

(−) 4,5,5a,6,7,8-hexahydro-6-propyloxazolo[5,4-f]quinolin-2-amine;

(±) 4,5,5a,6,7,8-hexahydro-6-propyloxazolo[4,5-f]quinolin-2-amine;

(+) 4,5,5a,6,7,8-hexahydro-6-propyloxazolo[4,5-f]quinolin-2-amine;

(−) 4,5,5a,6,7,8-hexahydro-6-propyloxazolo[4,5-f]quinolin-2-amine;

(±) trans-4,5,5a,6,7,8,9,9a-octahydro-6-propyloxazolo[4,5-f]quinolin-2-amine;

(±) trans-4,5,5a,6,7,8,9,9a-octahydro-6-propyloxazolo[5,4-f]quinolin-2-amine;

(±) 4,5,5a,6,7,8-hexahydro-6-methyl-1H(and 2H)pyrazolo[3,4-f]quinoline;

(+) 4,5,5a,6,7,8-hexahydro-6-methyl-1H(and 2H)pyrazolo[3,4-f]quinoline;

(−) 4,5,5a,6,7,8-hexahydro-6-methyl-1H(and 2H)pyrazolo[3,4-f]quinoline;

(±) 4,5,5a,6,7,8-hexahydro-6-propyl-1H(and 2H)pyrazolo[3,4-f]quinoline;

(+) 4,5,5a,6,7,8-hexahydro-6-propyl-1H(and 2H)pyrazolo[3,4-f]quinoline;

(−) 4,5,5a,6,7,8-hexahydro-6-propyl-1H(and 2H)pyrazolo[3,4-f]quinoline;

(±) 4,5,5a,6,7,8-hexahydro-6-(2-propenyl)-1H(and 2H)pyrazolo[3,4-f]quinoline;

(+) 4,5,5a,6,7,8-hexahydro-6-(2-propenyl)-1H(and 2H)pyrazolo[3,4-f]quinoline;

(−) 4,5,5a,6,7,8-hexahydro-6-(2-propenyl)-1H(and 2H)pyrazolo[3,4-f]quinoline;

(±) trans-4,5,5a,6,7,8,9,9a-octahydro-6-propyl-1H (and 2H)pyrazolo[3,4-f]quinoline;

(±) 4,5,5a,6,7,8-hexahydro-6-propyl-1H(and 2H)pyrazolo[4,3-f]quinoline;

(+) 4,5,5a,6,7,8-hexahydro-6-propyl-1H(and 2H)pyrazolo[4,3-f]quinoline;

(−) 4,5,5a,6,7,8-hexahydro-6-propyl-1H(and 2H)pyrazolo[4,3-f]quinoline;

(±) 5,6,6a,7,8,9-hexahydro-7-propyl-4H-thiazolo[4′,5′:3,4]cyclohepta[1,2-b]pyridin-2-amine;

(±) 5,6,6a,7,8,9,10,10a-octahydro-7-propyl-4H-thiazolo[4′,5′:3,4]cyclohepta[1,2-b]

or a pharmaceutically acceptable acid addition salt thereof.

The compounds of formula I are valuable dopaminergic agents. The tests employed indicate that compounds of formula I possess dopamine agonist activity with selectivity for the presynaptic dopamine receptor (autoreceptor). Thus, the compounds of formula I were tested for their ability to inhibit locomotor activity in mice according to the assay described in *Pharmacol. Biochem. Behav.* 1978 (8) 97; for their ability to inhibit haloperidol binding in a receptor binding assay described in *Mol. Pharmacol.* 1976 (12) 800; and for their ability to inhibit dopamine synthesis in rats according to the protocol described in *Naumyn-Schmiedeberg's Arch. Pharmacol.*, 1976 (296) 5. The above test methods are incorporated herein by reference. The data in the table shows the selective presynaptic dopamine agonist activity of representative compounds of formula I.

The compounds of the present invention may be prepared by various methods using synthetic steps known in the literature.

Thus, for example, the compounds of formula II may be prepared according to Scheme 1:

TABLE

Biological Activity of Compounds of Formula I

| Example Number | Compound | Inhibition of Locomotor Activity in Mice (ED$_{50}$, mg/kg, IP) | Percent Inhibition of Haloperidol Binding | Pecent Inhibition of Dopamine Synthesis |
|---|---|---|---|---|
| 40 | (±) 4,5,5a,6,7,8-Hexahydrothiazolo[4,5-f]quinolin-2-amine | 11.6 | 77 at 5 × 10$^{-6}$ M | 44 at 10 mg/kg |
| 5a | (±) 4,5,5a,6,7,8-Hexahydro-6-methylthiazolo[4,5-f]quinolin-2-amine | 2.6 | 62 at 5 × 10$^{-6}$ M | 92 at 10 mg/kg |
| 5b | (±) 6-Ethyl-4,5,5a,6,7,8-hexahydrothiazolo[4,5-f]quinolin-2-amine | 0.62 | 68 at 5 × 10$^{-6}$ M | 60 at 1 mg/kg |
| 5 | (±) 4,5,5a,6,7,8-Hexahydro-6-propylthiazolo[4,5-f]quinolin-2-amine | 5.5 | 43 at 1 × 10$^{-6}$ M | 53 at 5 mg/kg |
| 5c | (±) 6-Butyl-4,5,5a,6,7,8-hexahydrothiazolo[4,5-f]quinolin-2-amine | 14.7 | 70 at 1 × 10$^{-5}$ M | 18 at 10 mg/kg |
| 5d | (±) 4,5,5a,6,7,8-Hexahydro-6-(2-propenyl)thiazolo[4,5-f]quinolin-2-amine | 0.24 | 69 at 5 × 10$^{-7}$ M | 100 at 5 mg/kg |
| 5e | (±) 6-(Cyclopropylmethyl)-4,5,5a,6,7,8-hexahydrothiazolo[4,5-f]quinolin-2-amine | 12.0 | 62 at 1 × 10$^{-6}$ M | |
| 5f | (±) 4,5,5a,6,7,8-Hexahydro-6-(2-phenylethyl)thiazolo[4,5-f]quinolin-2-amine | 31.3 | 67 at 5 × 10$^{-6}$ M | |
| 5g | (±) 4,5,5a,6,7,8-Hexahydro-6-(phenylmethyl)thiazolo[4,5-f]quinolin-2-amine | 26.1 | 61 at 5 × 10$^{-6}$ M | |
| 15a | (±) N—(4,5,5a,6,7,8-Hexahydro-6-propylthiazolo[4,5-f]quinolin-2-yl)acetamide | 16.3 | 23 at 5 × 10$^{-6}$ M | |
| 15b | (±) N—[4,5,5a,6,7,8-Hexahydro-6-(2-propenyl)thiazolo[4,5-f]quinolin-2-yl]acetamide | 3.1 | 21 at 1 × 10$^{-5}$ M | 82 at 5 mg/kg |
| 16 | (±) 4,5,5a,6,7,8-Hexahydro-6-propylthiazolo[4,5-f]quinolin-2-amine | 2.5 | 76 at 5 × 10$^{-6}$ M | 100 at 3 mg/kg |
| 17 | (±) trans-4,5,5a,6,7,8,9,9a-Octahydro-6-propylthiazolo[5,4-f]quinolin-2-amine | 0.7 | 37 at 1 × 10$^{-6}$ M | 100 at 1 mg/kg |

Scheme 1

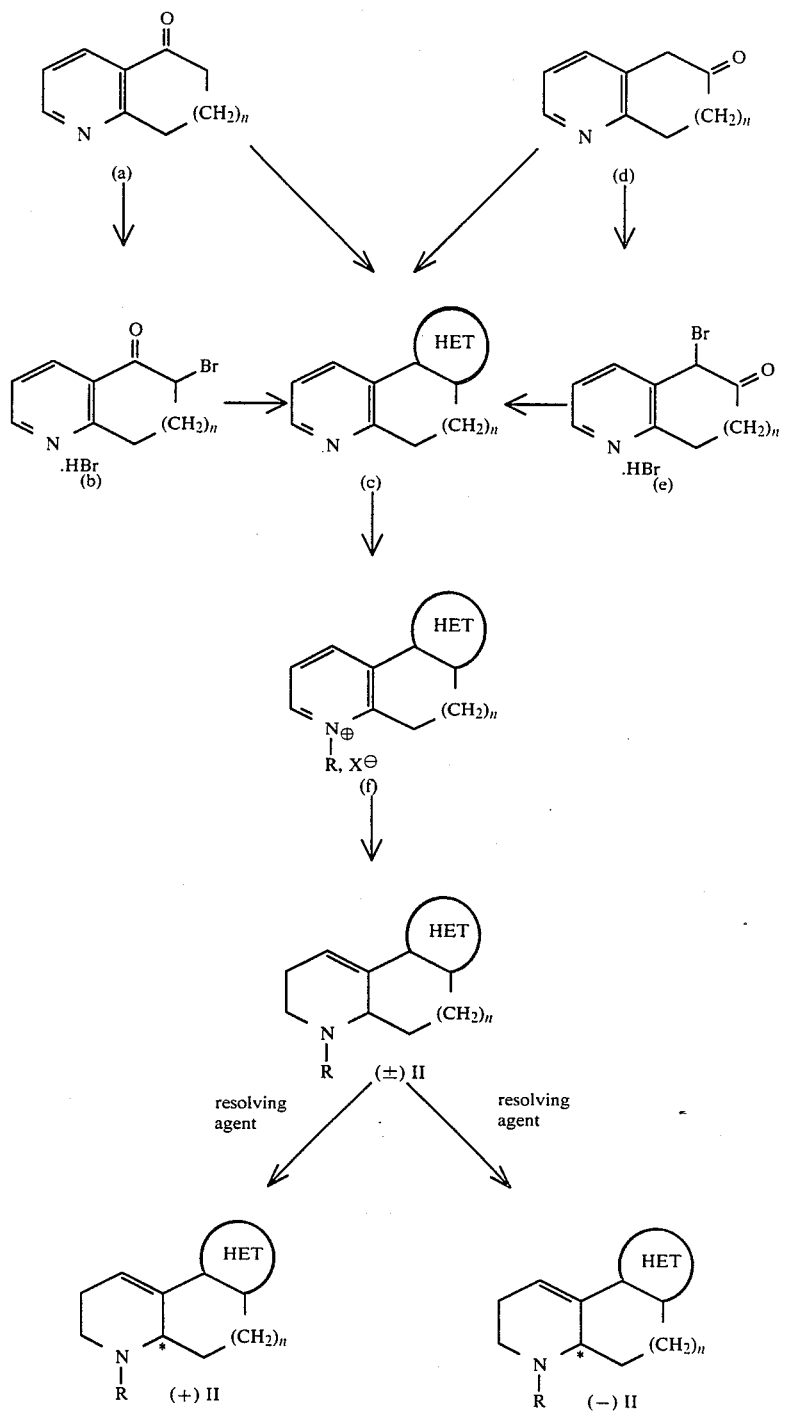

*indicates asymmetric carbon atom

Compounds of formula (a) in Scheme 1 are either known or capable of being prepared by methods known in the art. Bromination by usual means proceeds at the methylene group adjacent to the carbonyl group to afford a compound of formula (b) as the hydrobromide salt when excess 48% hydrobromic acid is used. A compound of formula (b) is reacted with a compound of formula

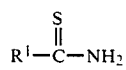

in which $R^1$ is as defined above, to afford a compound of formula

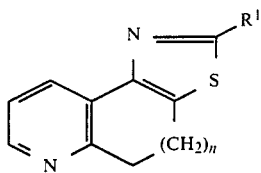

in which R¹ and n are as defined above. A quaternary halide salt is then prepared by reaction of the previous intermediate with R—X, in which R is alkyl, alkenyl, cycloalkylalkyl or arylalkyl, and X is halide, e.g., chloride, bromide or iodide. The resulting salt is reduced with a complex metal hydride, such as sodium borohydride to afford a compound of formula (±) II¹

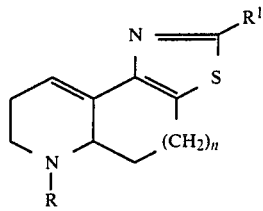

(±) II¹ in which R is alkyl, alkenyl, cyloalkylalkyl, or arylalkyl, and R¹ and n are as defined above.

Compounds of formula (d) in Scheme 1 are either known or capable of being prepared by methods known in the art. Bromination, reaction with a compound of formula

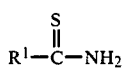

in which R¹ is as defined above, followed by quaternization and reduction with a complex metal hydride as described above affords other thiazole derivatives of formula (±) II²

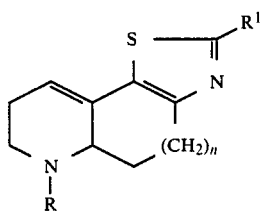

(±) II² in which R is alkyl, alkenyl, cycloalkylalkyl, or arylalkyl, and R¹ and n are as defined above.

Reaction of a compound of formula (a) in Scheme 1 with tris(dimethylamino)methane affords a compound of formula

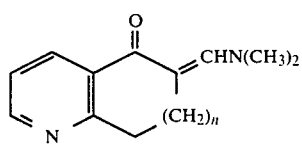

in which n is as defined above. Subsequent reaction of this intermediate with an amidine of formula

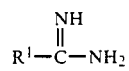

in which R¹ is as defined above affords a compound of formula

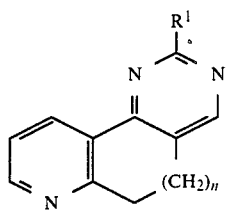

in which R¹ and n are as defined above. Quaternization of the above intermediate and reduction with a complex metal hydride as previously described affords pyrimidino derivatives of formula (±) II³

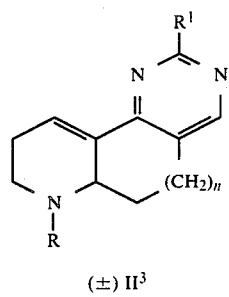

(±) II³ in which R is alkyl, alkenyl, cycloalkylalkyl, or arylalkyl, and R¹ and n are as defined above.

Reaction of a compound of formula (d) in Scheme 1 with tris (dimethylamino) methane, followed by reaction with an amidine of formula

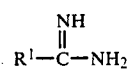

in which R¹ is as defined above affords a compound of formula

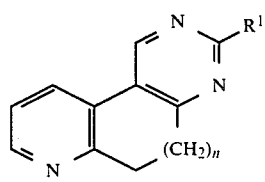

in which R¹ and n are as defined above. Quaternization of this intermediate and reduction with a complex metal hydride as described above affords other pyrimidino derivatives of formula (±) II⁴

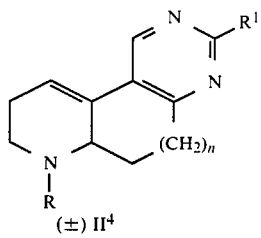

(±) II⁴ in which R is alkyl, alkenyl, cycloalkylalkyl, or arylalkyl, and R¹ and n are as defined above.

Reaction of a compound of formula (b) in Scheme 1 with a compound of formula

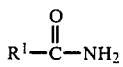

in which R¹ is NH₂ or Nr³R⁴ affords a mixture of compounds of formulas

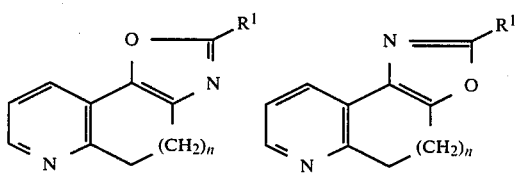

in which R¹ is NH₂ or NR³R⁴, and n, R³ and R⁴ are as defined above. Chromatographic separation of the above mixture, quaternization and reduction with a complex metal hydride of each of the compounds as described above affords the two oxazole derivatives of formula (±) II⁵ and formula (±) II⁶, respectively

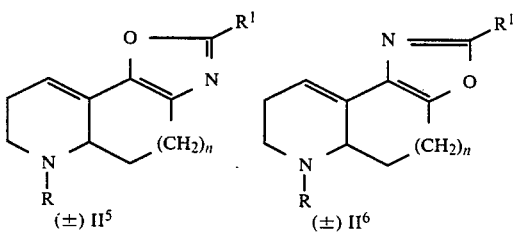

(±) II⁵    (±) II⁶ in which R is alkyl, alkenyl, cycloalkylalkyl, or arylalkyl, and R¹ is NH₂ or NR³R⁴ and n, R³ and R⁴ are as defined above.

Reaction of a compound of formula (b) in Scheme 1 with a compound of formula

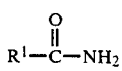

in which R¹ is hydrogen or alkyl affords a compound of formula

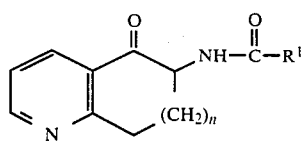

in which R¹ is hydrogen or alkyl and n is as defined above. Subsequent reaction with concentrated sulfuric acid or phosphorous pentachloride affords a compound of formula

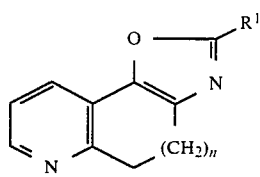

in which R¹ is hydrogen or alkyl and n is as defined above. Quaternization and reduction with a complex metal hydride as described above affords a compound of formula (±) II⁵

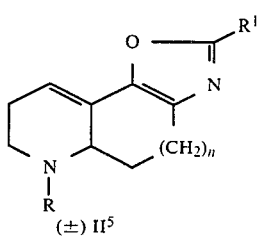

(±) II⁵ in which R is alkyl, alkenyl, cycloalkylalkyl, or arylalkyl, and R¹ is hydrogen or alkyl and n is as defined above.

Reaction of a compound of formula (e) in Scheme 1 with a compound of formula

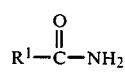

in which R¹ is hydrogen or alkyl affords a compound of formula

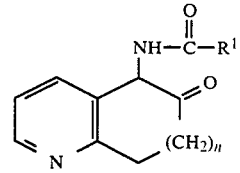

in which R¹ is hydrogen or alkyl and n is as defined above. Subsequent reaction with concentrated sulfuric acid or phosphorous pentachloride affords a compound of formula

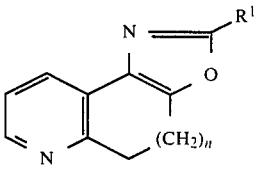

in which R¹ is hydrogen or alkyl and n is as defined above. Quaternization and reduction with a complex metal hydride as described above affords a compound of formula (±) II⁶

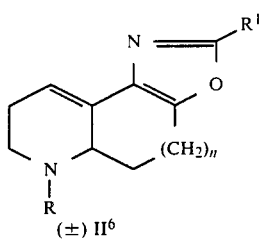

in which R is alkyl, alkenyl, cycloalkylalkyl, or arylalkyl, and $R^1$ is hydrogen or alkyl and n is as defined above.

Reaction of a compound of formula (a) in Scheme 1 with a base such as, for example, potassium tertiary butoxide or sodium methoxide and ethyl formate and subsequent reaction with hydrazine affords a compound of formula

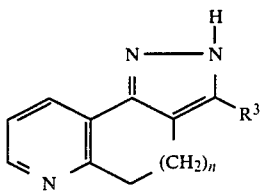

in which $R^3$ is hydrogen and n is as defined above.

A compound in which $R^3$ in the previous structure is an alkyl group is obtained by reacting a compound of formula (a) with a base, such as, for example lithium diisopropylamide and the like and an acid chloride of the formula

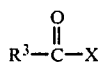

in which X is a halogen, such as for example chlorine or bromine, and $R^3$ is as defined above. Subsequent reaction with hydrazine, quaternization and reduction with a complex metal hydride affords a pyrazolo derivative of formula $(\pm)$ $II^7$

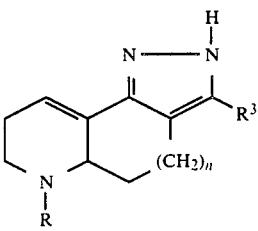

in which R is alkyl, alkenyl, cycloalkylalkyl, or arylalkyl, and $R^3$ and n are as defined above.

Reaction of a compound of formula (d) in Scheme 1 with a base and ethyl formate or alternatively a base and an acid chloride of the formula

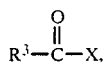

followed by reaction with hydrazine, quaternization and reduction with a complex metal hydride as described above affords other pyrazolo derivatives of formula $(\pm)$ $II^8$

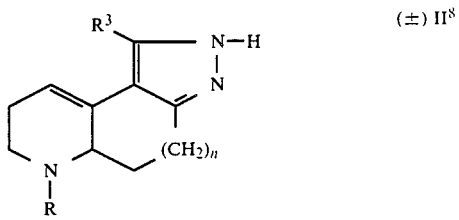

in which R is akyl, alkenyl, cycloalkylalkyl, or arylalkyl, and $R^3$ and n are as defined above.

Pyrazolo derivatives represented by the above structures are tautomers such as, for example, in a compound of formula $(\pm)$ $II^7$

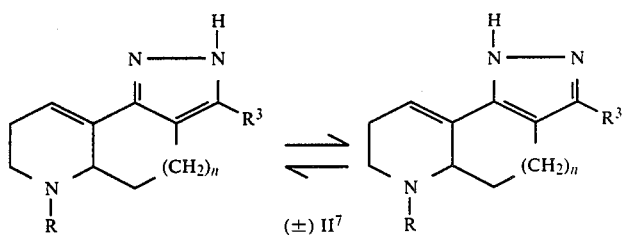

there is a dynamic equilibrium between the above structures. It is understood that when a single member of a tautomeric pair is described the other tautomer is also described thereby.

According, the present invention provides a method of preparing a compound of formula $(\pm)$ II which comprises reducing a compound of formula

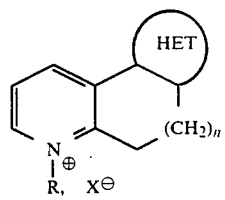

in which R is alkyl, alkenhl, cycloalkylalkyl, or arylalkyl, X is chloride, bromide or iodide, and HET and n are as define above with a complex metal hydride in an inert solvent.

Inert solvents used in the reduction step will depend on the hydride used. Examples of solvents are diethyl ether, tetrahydrofuran, diglyme (diethylene-glycol dimethyl ether), alcohols, e.g. methanol and mixtures of alcohols and water, e.g. methanol and water.

A compound of formula $(\pm)$II in which R is hydrogen and HET and n are as defined above is prepared, in the conventional manner, by demethylation of a compound of formula

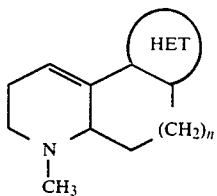

in which HET and n are as defined above with, for example, cyanogen bromide, followed by hydrolysis with an acid such as hydrochloric acid.

Further, a compound of forumula (±) II in which R is

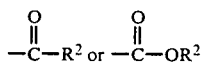

wherein $R^2$, HET and n are as defined above is prepared, in the conventional manner, by contacting the previous compound of formula (±) II in which R is hydrogen and HET and n are as defined above with a compound of formula

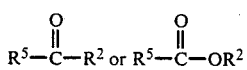

in which $R^5$ is a halogen such as chlorine or bromine or another leaving group and $R^2$ is as defined above.

The reaction is carried out in a nonaqueous solvent such as acetonitrile, tetrahydrofuran or methylene chloride, preferably methylene chloride, with an added organic base such as triethylamine.

Compounds of formulas

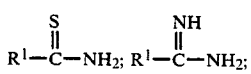
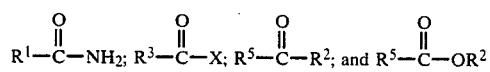

are either known or capable of being prepared by methods known in the art.

A compound of formula (±) II in Scheme 1 is a racemic mixture. The * in Scheme 1 indicates the position of the asymmetric carbon atom. Accordingly, as another aspect of the present invention, a compound of formula (±) II may be resolved into its enantiomers by the use of optically active acids. When $R^1$ is $NH_2$ a compound of formula (±) II is first converted to its isobutyramide derivative. The isobutyramide derivative is reacted with an optically active acid, such as, for example (+) or (−) 1,1'-binaphthyl-2,2'-diylhydrogen phosphate, (+) or (−) di-p-toluoyltartaric acid, and the like. Separation of the resulting diastereomeric salts by crystallization followed by neutralization and hydrolysis of the amide group affords the optically active enantiomer (+) II or (−) II.

The compounds of formulas III and IV are prepared according to Scheme 2:

Scheme 2

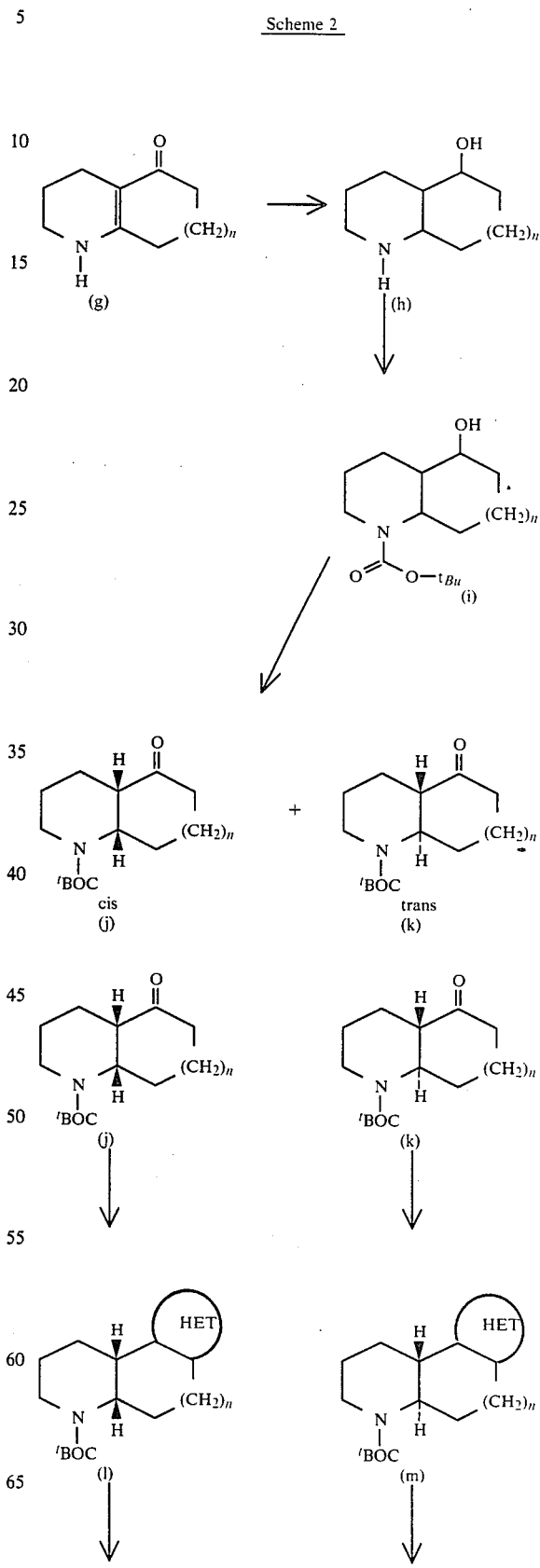

-continued
Scheme 2

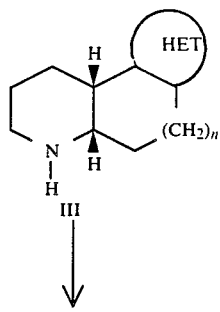
III

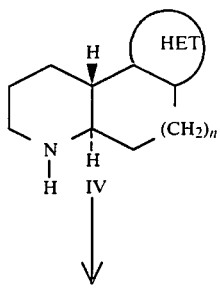
IV

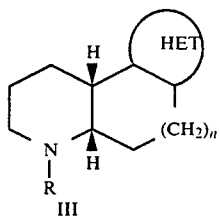
III

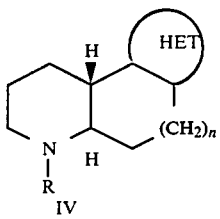
IV

Compounds of formula (h) in Scheme 2 are either known or capable of being prepared by methods known in the art from compounds of formula (g). A compound of formula (h) is blocked with a tertiary butoxycarbonyl group, also described as t-BOC, to a compound of formula (i). Oxidation of a compound of formula (i) with, for example, pyridine dichromate affords a mixture of cis and trans compounds of formulas (j) and (k). These isomers are separated by chromatographic methods and then each converted by the same series of steps to the desired products III and IV. The series of steps resembles the methods previously described to prepare the thiazolo, pyrimidino, oxazolo and pyrazolo fused ring systems in the synthesis of compounds of formula II.

Accordingly, bromination at the alpha (adjacent) position to the carbonyl group in a compound of formula (k) followed by reaction with a compound of formula

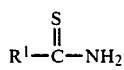

in which R¹ is as defined above, and subsequent removal of the tertiary butoxycarbonyl blocking group (t-BOC) by conventional means, e.g., acid hydrolysis, provides a compound of formula IV¹ (trans)

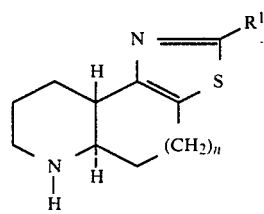
IV¹ in which R¹ and n are defined above.
A compound of formula IIII¹ (cis)

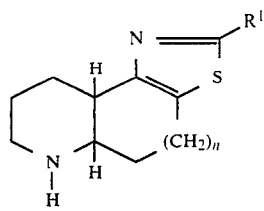
III¹ in which R¹ and n are as defined above is prepared from a compound of formula (j) in Scheme 2 by following the same procedure used to prepare a compound of formula IV¹ (trans).

Reaction of a compound of formula (o)

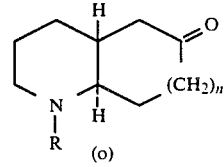
(o)

in which R and n are as defined above with a compound of formula

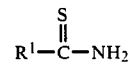

in which R¹ is as defined above, and iodine provides a compound of formula IV² (trans)

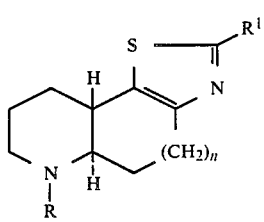
IV² in which R, R¹, and n are as defined above.
A compound of formula III² (cis)

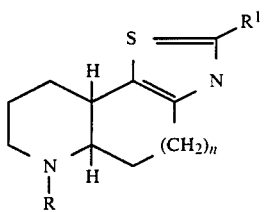
III² in which R, R¹ and n are as defined above is prepared from the cis ketone of formula (p)

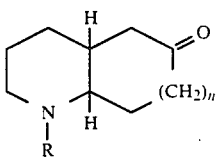
(p)

in which R and n are as defined above following the same procedure used to prepare a compound of formula IV² (trans).

Compounds of formula (o) or (p) are either known or capable of being prepared by methods known in the art.

Reaction of a compound of formula (k) in Scheme 2 with tris (dimethylamino)methane affords a compound of formula

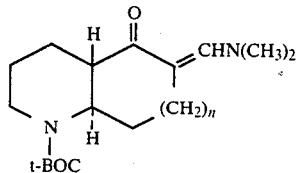

in which n is as defined above.

Reaction of the previous intermediate with an amidine of formula

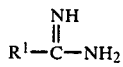

in which R¹ is as defined above, followed by removal of the t-BOC group with acid as described above affords a compound of formula IV³ (trans)

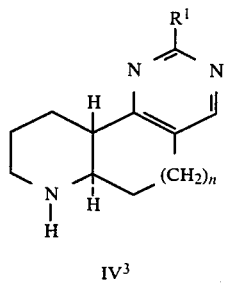

IV³ in which R¹ and n are as defined above.

A compound of formula III³ (cis)

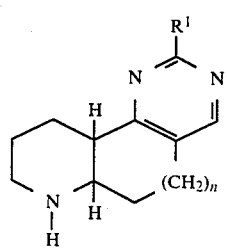

III³ in which R¹ and n are as defined above is prepared from a compound of formula (j) in Scheme 2 by following the same procedure used to prepare a compound of formula IV³ (trans).

Reaction of a compund of formula (q)

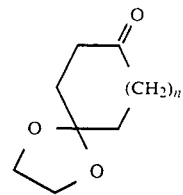

(q)

in which n is as defined above with tris(dimethylamino)methane affords a compound of formula

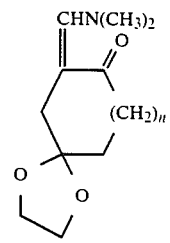

in which n is as defined above.

Reaction of this intermediate with an amidine of formula

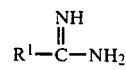

in which R¹ is as defined above affords a compound of formula

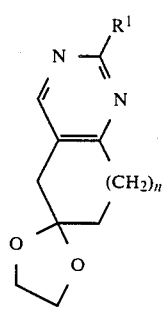

in which R¹ and n are as defined above.

Removal of the carbonyl protecting group of this intermediate with an acid such as, for example, trifluoroacetic acid, followed by reaction with acrylamide affords a compound of formula (r)

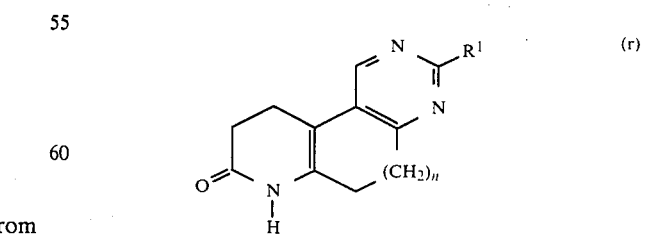

in which R¹ and n are as defined above.

Reaction of a compund of the formula (r) with triethylsilane and trifluoroacetic acid affords a compound of formula (s) (trans)

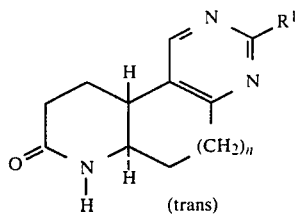

(s) (trans)

in which R¹ and n are as defined above.

Reaction of a compound of formula (s) with diborane in tetrahydrofuran affords a compound of formula IV⁴ (trans)

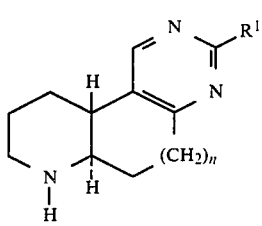

IV⁴ in which R¹ and n are as defined above.

A compound of formula III⁴ (cis)

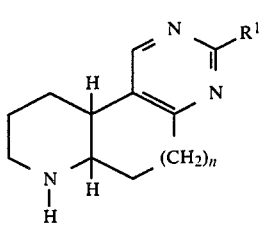

III⁴ in which R¹ and n are as defined above is prepared by converting a compound of formula (r) to a compound of formula (s) (cis)

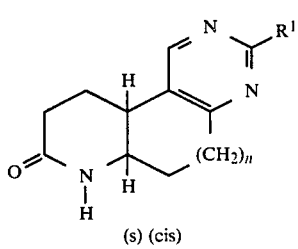

(s) (cis)

in which R¹ and n are as defined above and subsequently using the same procedure as described for preparing a compound of formula IV⁴ (trans).

Compounds of formula (q) are either known or capable of being prepared by methods known in the art.

Bromination at the alpha (adjacent) position to the carbonyl group in a compound of formula (k) in Scheme 2 as described above followed by reaction with a compound of formula

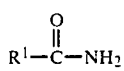

in which R¹ is as defined above and subsequent removal of the t-BOC group as described above affords a mixture of compounds of formulas IV⁵ (trans) and IV⁶ (trans)

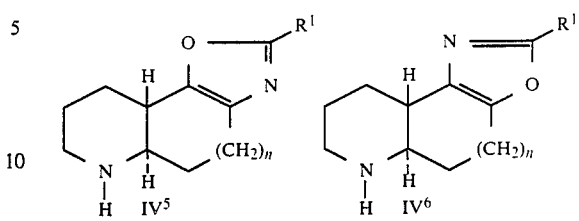

in which R¹ and n are as defined above. The mixture of compounds of formulas IV⁵ (trans) and IV⁶ (trans) is separated by chromatographic methods.

A mixture of compounds of formulas III⁵ (cis) and III⁶ (cis)

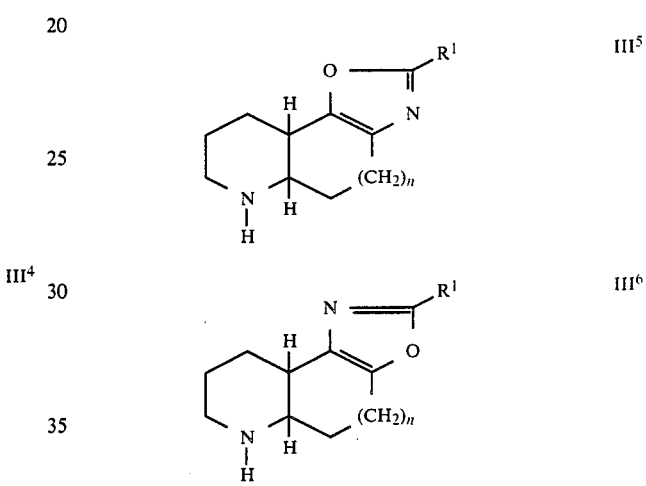

in which R¹ and n are as defined above is prepared from a compound of formula (j) in Scheme 2 by following the same procedure used to prepare compounds of formula IV⁵ (trans) and IV⁶ (trans). The individual compounds are then separated by chromatographic methods.

Reaction of a compound of formula (k) in Scheme 2 with a base such as, for example, potassium tertiary butoxide or sodium methoxide and ethyl formate, followed by reaction with hydrazine and subsequent removal of the t-BOC group with acid as described above affords a compound of formula IV⁷ (trans)

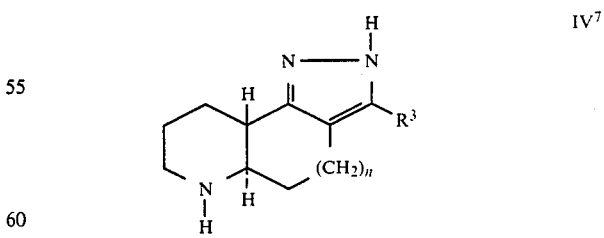

in which R³ is hydrogen and n is as defined above.

A compound of the formula IV⁷ (trans) in which R³ is an alkyl group is obtained by reacting a compound of formula (k) in Scheme 2 with a base, such as, for example, lithium diisopropylamide and an acid chloride of the formula

in which R³ is alkyl and X is as defined above, followed by reaction with hydrazine and subsequent removal of the t-BOC group as described above to afford a compound of formula IV⁷ (trans) in which R³ is alkyl and n is as defined above.

A compound of formula III⁷ (cis)

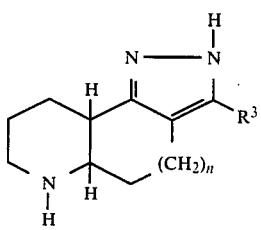

in which R³ and n are as defined above is prepared from a compound of formula (j) in Scheme 2 by following the same procedure used to prepare a compound of formula IV⁷ (trans).

As described previously for a compound of formula II, compounds of formula III⁷ or IV⁷ exist in tautomeric pairs.

Accordingly, the present invention provides a method of preparing a compound of formula III (cis) or formula IV (trans) which comprises removing the t-BOC blocking group with acid from a compound of the formula (l) (cis) or formula (m) (trans)

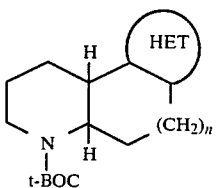

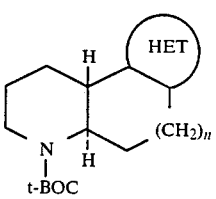

in which HET and n are as defined above.

For the removal of the t-BOC group acids such as for example, trifluoroacetic acid, hydrochloric acid, and the like may be used in the presence of an inert solvent or solvents such as for example, dichloromethane, chloroform, diethyl ether, and the like preferably trifluoroacetic acid in chloroform.

Alternatively, a compound of formula III (cis) or formula IV (trans) may be prepared by reducing a compond of formula (t) (cis) or (u) (trans)

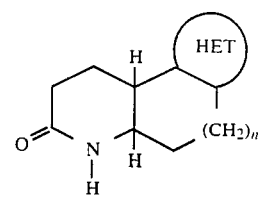

or

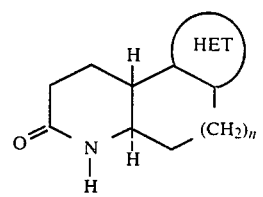

in which HET and n are as defined above with a reducing agent such as a complex metal hydride.

A compound of formula (t) and formula (u) can be prepared from the same intermediate of formula (v).

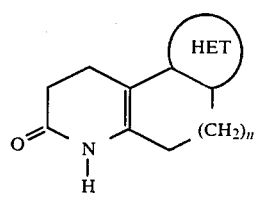

A compound of formula (v) can be prepared from a compound of formula (w)

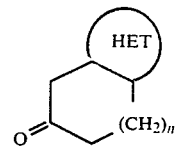

Thus, formation of the enamine of a compound of formula (w) by reaction with a secondary aliphatic amine, such as for example pyrrolidine, in an inert solvent, such as for example toluene or benzene, in the presence of a catalytic amount of an acid, such as for example para-toluenesulfonic acid, followed by reaction of the enamine with acrylamide in the absence of solvent or in an inert solvent, such as for example, N,N-dimethylformamide, at a temperature of about 100° C., affords a compound of formula (v). Catalytic hydrogenation of a compound of formula (v) (u) (trans). Compounds of formula (w) are prepared by methods known in the art.

To synthesize compounds of formula III or IV where R is other than hydrogen, alkylation of the unsubstituted compound (R═H) by conventional means with the appropriate halide, R—X, wherein R is alkyl, alkenyl, cycloalkylalkyl or arylalkyl and X is chloro, bromo or iodo, affords the desired products.

The base used in the alkylation step is preferably an alkaline hydroxide such as potassium or sodium hydroxide. The alkylation is also preferably carried out at elevated temperatures, e.g., the boiling point of the solvent, which is preferably an alcohol, e.g. methanol or ethanol.

To synthesize compounds of formula III or IV where R is

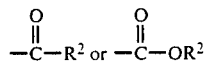

acylation of the unsubstituted compound (R=H) by conventional means with a compound of formula

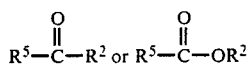

in which $R^5$ is a halogen such as chlorine or bromine or another leaving group and $R^2$ is as defined above, affords the desired product.

A compound of formula III (cis) or formula IV (trans) is a racemic mixture. Accordingly, as another aspect of the present invention, a compound of formula III (cis) or formula IV (trans) may be resolved into its enantiomers by the use of optically active acids as described previously for a compound of formula II.

Compounds of formula I, prepared as above described, may if desired, be converted to pharmaceutically acceptable acid addition salts by conventional means where the free base is treated with the desired acid selected from those defined above.

The compounds of the present invention can be prepared and administered in a wide variety of oral and parenteral dosage forms. It will be obvious to those skilled in the art that the following dosage forms may comprise as the active component, either a compound of formula I, a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet, the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low-melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate numbe of any of these packaged forms.

The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 0.1 mg to about 10 mg per kilogram daily. A daily dose range of about 1.0 mg to about 10 mg per kilogram is preferred.

The dosages, however, may be varied depending upon the requirements of the patients, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors preferred methods for preparing the compounds of the invention.

EXAMPLE 1

7,8-Dihydro-5(6H)-quinolinone

The procedure of Rimek and Zymalkowski (*Arch. Pharm.* 1961, 294, 759–765) was followed. Over a period of 1 hour, 40.9 g (0.757 mol) of freshly-distilled propiolaldehyde was added dropwise to a solution of 42.1 g (0.379 mol) of 3-amino-2-cyclohexenone in 1.5 l of N,N-dimethylformamide (DMF). The solution was stirred at room temperature for 12 hours. The DMF was evaporated at reduced pressure. Vacuum distillation (bp 60°–65° C. at 0.025–0.050 mmHg) of the resultant black tars gave 30.2 g (54.2%) of 7,8-dihydro-5(6H)-quinolinone as a colorless liquid.

EXAMPLE 2

6-Bromo-7,8-dihydro-5(6H)-quinolinone, hydrobromide

To a warm solution of 5.00 g (33.52 mmol) of 7,8-dihydro-5(6H)-quinolinone, prepared in Example 1, in 25 ml of 48% hydrobromic acid, was added dropwise 6.0 g (37.54 mmol) of bromine. The solution was stirred at room temperature for 1 hour, then concentrated to a yellow-white solide. Recrystallization from absolute ethanol afforded 9.20 g (88.5%) of 6-bromo-7,8-dihydro-5(6H)-quinolinone hydrobromide as a white solid; mp 187°–189° C. (dec.).

EXAMPLE 3

4.5-Dihydrothiazolo[4,5-f]quinoline-2-amine

A solution of 12.6 g (41.04 mmol) of 6-bromo-7,8-dihydro-5(6H)-quinolinone, hydrobromide, obtained in Example 2, and 3.44 g (45.19 mmol) of thiourea in 100 ml of distilled water was refluxed gently for 30 minutes. The solution was cooled and upon basification with 5% ammonium hydroxide a solid formed. The mixture was cooled and filtered. The solid was washed with ice-cold water and recrystallized from acetonitrile, affording 5.29 g (63.4%) of the title compound as an orange-brown solid, mp 210°–260° C. (dec.). Microanalysis and spectral data were consistent with the structure.

EXAMPLE 4

2-Amino-4,5-dihydro-6-propylthiazolo[4,5-f]quinolinium iodide

To a refluxing solution of 2.00 g (9.84 mmol) of 4,5-dihydrothiazolo[4,5-f]quinolin-2-amine, obtained in Example 3, in 200 ml of acetonitrile was added 10 ml (102.54 mmol) of 1-iodopropane. The solution was refluxed for 12 hours, during which time a precipitate formed and the color turned bright yellow. More 1-iodopropane (10 ml) was added and the mixture was refluxed for another 12 hours. The mixture was filtered hot, the bright yellow solid was washed with acetonitrile and vacuum dried to give 2.65 g (72.2%) of the title compound.

EXAMPLE 5

(±)
4,5,5a,6,7,8-Hexahydro-6-propylthiazolo[4,5-f]quinolin-2-amine

An ice-cold suspension of 2.55 g (6.83 mmol) of 2-amino-4,5-dihydro-6-propylthiazolo[4,5-f]-quinolinium iodide, obtained in Example 4, in 100 ml of a mixture of methanol and water (1:1) was treated with 2.6 g (67.41 mmol) of sodium borohydride, in small portions over a period of 30 minutes. The suspension was stirred at 0° C. for 3 hours, then at room temperature overnight. The suspension was cooled, quenched with 6N hydrochloric acid to pH of 1, concentrated in-vacuo to remove the methanol and the residue was partitioned between 5% ammonium hydroxide and methylene chloride. The organic layer was dried over magnesium sulfate, filtered and concentrated to a brown solid. Medium pressure chromatography (silica gel, 2% ammonium hydroxide 98% ethyl acetate) of the crude solid afforded 0.60 g (35.3%) of the title compound as a light tan solid; mp 146°–149° C.

The dihydrochloride salt, mp 269°–270° C., was also prepared.

In a process analogous to Example 5 using appropriate starting materials, the corresponding compounds of formula I are prepared as follows:

EXAMPLE 5a (±)
4,5,5a,6,7,8-Hexahydro-6-methylthiazolo[4,5-f]quinolin-2-amine mp 193°–195° C.

EXAMPLE 5b (±)
6-Ethyl-4,5,5a,6,7,8-hexahydrothiazolo[4,5-f]quinolin-2-amine mp 142°–145° C.

EXAMPLE 5c (±)
6-Butyl-4,5,5a,6,7,8-hexahydrothiazolo[4,5-f]quinolin-2-amine, dihydrochloride, hemihydrate mp 263°–265° C.

EXAMPLE 5d (±) 4,5,5a,6,7,8-Hexahydro-6-(2-propenyl)thiazolo [4,5-f]quinolin-2-amine, dihydrochloride mp 265°–267° C.

EXAMPLE 5e (±)
6-(Cyclopropylmethyl)-4,5,5a,6,7,8-hexahydrothiazolo[4,5-f]quinolin-2-amine, dihydrochloride mp 253°–259° C.

EXAMPLE 5f (±) 4,5,5a,6,7,8-Hexahydro-6-(2-phenylethyl)thiazolo [4,5-f]quinolin-2-amine mp 182°–183° C.

EXAMPLE 5g (±) 4,5,5a,6,7,8-Hexahydro-6-(phenylmethyl)thiazolo [4,5-f]quinolin-2-amine, dihydrochloride, hydrate mp 263°–265° C.

EXAMPLE 6

Decahydro-5-quinolinol

The procedure of Grob et al. (*Helv. Chim. Acta* 1965, 48, 799–808) was followed. A solution of 66.70 g (0.441 mol) of 2,3,4,6,7,8-hexahydro-5(1H)-quinolinone in 250 ml of glacial acetic acid containing 2 g of $PtO_2$ was hydrogenated at 450 psi and 50° C. for 75 hours. Hydrogen uptake was only 57.2% of the theoretical. The sample was filtered, concentrated (to remove most of the acetic acid), cooled to 0° C., basified with 6N sodium hydroxide to a pH of 12 and extracted three times with 500 ml of methylene chloride. The combined methylene chloride extract was dried over magnesium sulfate, filtered and concentrated to give 24.80 g (36.2%) of decahydro-5-quinolinol, which was a three component isomeric mixture by gas chromatography (GC) analysis, as a light brown oily-solid. This mixture was carried on to the next step without further purification.

EXAMPLE 7

Octahydro-5-hydroxy-1(2H)-quinolinecarboxylic acid, 1,1-dimethylethyl ester

To a solution of 24.80 g (0.160 mol) of the amino alcohol, obtained in Example 6, in 1 l of a mixture of tetrahydrofuran (THF) and water (1:1) was added 1.2 equivalents of 6N sodium hydroxide, 32 ml (0.192 mol), followed by dropwise addition of 1.2 equivalents, 41.8 g (0.192 mol) of di-t-butyl-dicarbonate in 250 ml of THF. The mixture was stirred at room temperature under nitrogen for 12 hours, then extracted with four 500 ml portions of diethyl ether. The combined diethyl ether extracts were dried over magnesium sulfate, filtered and concentrated to give 82.83 g of a yellow viscous oil. Medium pressure chromatography (silica gel, 20% ethyl acetate-80% iso-octane) of the crude oil afforded 39.14 g (96%) of octahydro-5-hydroxy-1(2H)-quinolinecarboxylic acid, 1,1-dimethylethyl ester as a colorless liquid.

EXAMPLE 8 cis and trans-Octahydro-5-oxo-1(2H)-quinolinecarboxylic acid, 1,1-dimethylethyl ester A suspension of 39.14 g (0.153 mol) of the alcohol, obtained in Example 7, and 346.0 g (0.920 mol) of pyridine dichromate in 1.5 l of methylene chloride was mechanically stirred at room temperature under nitrogen for 72 hours. The suspension was filtered through a pad of Celite, concentrated, suspended into 250 ml of diethyl ether and again filtered through a pad of Celite. The filtrate was concentrated to 34.81 g of a brown oil. Medium pressure chromatography (silica gel, 20% ethyl acetate—80% iso-octane) afforded 14.38 g (37%) of trans-octahydro-5-oxo-1(2H)-quinolinecarboxylic acid, 1,1-dimethylethyl ester ($R_f$ 0.43, silica gel, 50% ethyl acetate-50% iso-octane) as a low melting white solid and 12.16 g (31.1%) of cis-octahydro-5-oxo-1(2H)-quinoline carboxylic acid, 1,1-dimethylethyl ester ($R_f$ 0.34, silica gel, 50% ethyl acetate-50% iso-octane) as a colorless oil.

EXAMPLE 9

(±) cis-2-Amino-5,5a,7,8,9,9a-hexahydrothiazolo[4,5-f]quinoline-6(4H)-carboxylic acid, 1,1-dimethylethyl ester To a solution of lithium diisopropyl amide (5.88 mmol) in 10 ml of dry THF at −78° C. under nitrogen was added dropwise a solution of 1.00g (3.95 mmol) of cis-octahydro-5-oxo-1(2H)-quinolinecarboxylic acid, 1,1-dimethylethyl ester, obtained in Example 8, in 10 ml of THF. The solution was stirred at −78° C. for 3 hours, then treated with a solution of 0.85 ml (6.71 mmol) of chlorotrimethylsilane in 5 ml of THF. This solution was stirred at −78° C. for 2 hours, then allowed to warm to room temperature. The solution was concentrated to remove the THF, suspended into 25 ml of diethyl ether, filtered through a pad of Celite and reconcentrated to give 1.35 g of the silyl enol ether as a yellow oil.

A solution of the above silyl enol ether and 0.77 g (4.33 mmol) of N-bromosuccinimide in 25 ml of carbon tetrachloride was refluxed under nitrogen for 1 hour. The suspension was cooled, filtered through a pad of Celite and concentrated to give 1.82 g of the α-bromo ketone as a yellow-oil.

A solution of the above α-bromo ketone and 0.33 g (4.34 mmol) of thiourea in 50 ml of methanol was refluxed under nitrogen for 2 hours. The solution was concentrated, basified with saturated sodium bicarbonate solution and extracted into chloroform. The chloroform extract was dried over magnesium sulfate, filtered and concentrated to an oily yellow solid. The solid was washed with diethyl ether, filtered and vacuum dried affording 0.65 g (53.2%) of the title compound as a tan solid; mp 239°–240° C. (dec.).

EXAMPLE 10

(±) cis-4,5,5a,6,7,8,9,9a-Octahydrothiazolo[4,5-f]quinolin-2-amine, dihydrochloride To a solution of 1.00 g (3.23 mmol) of (±) cis-2-amino-5,5a,7,8,9,9a-hexahydrothiazolo[4,5-f]quinoline-6(4H)-carboxylic acid, 1,1-dimethylethyl ester (Example 9), in 50 ml of a mixture of methanol and chloroform (1:5) was added 12 ml (12 mmol) of hydrogen chloride (1.0M solution in diethyl ether). After stirring at room temperature under nitrogen for 12 hours, more hydrogen chloride (10 ml of a 1.0M solution in diethyl ether) was added and the mixture was stirred at room temperature for an additional 12 hours. The mixture was then concentrated to a solid, the solid was washed with diethyl ether, filtered and vacuum dried to give 0.89 g (97.8%) of the dihydrochloride salt of (±) cis-4,5,5a,6,7,8,9,9a-octahydrothiazolo[4,5-f]quinolin-2-amine, dihydrochloride, hemihydrate as a tan solid; mp 268°–271° C. (dec.).

EXAMPLE 11

(±) cis-4,5,5a,6,7,8,9,9a-Octahydro-6-propylthiazolo [4,5-f-quinolin-2-amine

A solution of the compound prepared in Example 10, 0.160 g (5.5 mmole), in 100 ml absolute ethanol was treated with finely ground potassium hydroxide, 1.12 g (20 mmol), and 1-iodopropane, 8.50 g (50 mmol). The resulting solution was heated at reflux, under an inert atmosphere, for 20 hours. The reaction mixture was concentrated in-vacuo and the residue was partitioned between dichloromethane and a 5% sodium bicarbonate solution. The organic phase was dried and evaporated in-vacuo, leaving 1.13 g (81.8%) of the title compound, which was converted to its dihydrochloride salt; mp 230°–232° C. (dec.).

EXAMPLE 12

(±) trans-2-Amino-5,5a,7,8,9,9a-hexahydrothiazolo [4,5-f]quinoline-6(4H)carboxylic acid, 1,1-dimethylethyl ester By applying the method of Example 9 to trans-octahydro-5-oxo-1(2H)-quinolinecarboxylic acid, 1,1-dimethylethyl ester, obtained in Example 8, the title compound was prepared as a tan solid; mp 227°–230° C. (dec.).

EXAMPLE 13

(±) trans-4,5,5a,6,7,8,9,9a-Octahydrothiazolo[4,5-f-]quinolin-2-amine, dihydrochloride By applying the method of Example 10 to the compound obtained in Example 12, the title compound was prepared as a white solid; mp 279°-282° C. (dec.).

EXAMPLE 14

(±) trans-4,5,5a,6,7,8,9,9a-Octahydro-6-propylthiazolo[4,5-f]quinolin-2-amine

Using the procedure of Example 11, 1.3 g of (±) trans-4,5,5a,6,7,8,9,9a-octahydrothiazolo[4,5-f]quinolin-2-amine dihydrochloride, obtained in Example 13, was transformed into the title compound (0.92 g, 80%) as a tan solid; mp 163°-181° C.

EXAMPLE 15

(±) N-4,5,5a,6,7,8-Hexahydro-6-methylthiazolo[4,5-f]quinolin-2-yl)-2-methylpropanamide A suspension of (±) 4,5,5a,6,7,8-hexahydro-6-methylthiazolo[4,5-f]quinolin-2-amine, 8.21 g (37.09 mmol), (Example 5a), and sodium isobutyrate, 11.23 g (102 mmol), in 100 ml isobutyric anhydride is heated at 100° C., under a nitrogen atmosphere, for 4 hours. The resulting solution is concentrated in-vacuo and the residue is partitioned between dichloromethane and 10% sodium bicarbonate solution. The organic phase is washed with brine, dried over magnesium sulfate and evaporated in-vacuo. The remaining semisolid residue is triturated with 50 ml diethyl ether to give 7.78 g of the title compound (72%) as an orange solid, mp 174°-184° C.

In a process analogous to Example 15, using appropriate starting materials, the corresponding compounds of formula I are prepared as follows:

EXAMPLE 15a (±) N-(4,5,5a,6,7,8-Hexahydro-6-propylthiazolo[4,5-f]quinolin-2-yl)acetamide mp 220°-231° C.

EXAMPLE 15b (±) N-[4,5,5a,6,7,8-Hexahydro-6-(2-propenyl)thiazolo[4,5-f]quinolin-2-yl]acetamide mp 226°-228° C.

EXAMPLE 15c (±) N-(4,5,5a,6,7,8-Hexahydro-6-propylthiazolo[4,5-f]quinolin-2-yl)-2-methylpropanamide mp 162°-165° C.

EXAMPLE 16

(±) 4,5,5a,6,7,8-Hexahydro-6-propylthiazolo[4,5-f]quinolin-2-amine, dihydrochloride 26.0 g of (±) N-(4,5,5a,6,7,8-hexahydro-6-propylthiazolo[4,5-f]quinolin-2-yl)-2-methylpropanamide, (Example 15c), is dissolved in 250 ml hot 95% ethanol and treated with a solution of 23.5 g (−)-ditoluoyl-L-tartaric acid hydrate in 100 ml hot 95% ethanol. The volume of the solution is reduced to 325 ml by boiling on a steam bath. Upon cooling to room temperature and scratching, a white salt begins to form. The flask is refrigerated for several hours and the salt filtered (weight=35.5 g). The salt is recrystallized from 185 ml 95% ethanol to yield 15.7 g of a white solid; mp 174°-175° C. The salt is partitioned between 2% ammonium hydroxide and ethyl acetate. The organic extract is evaporated in-vacuo and refluxed in 250 ml 10% hydrochloric acid for 5 hours. After cooling, concentrated ammonium hydroxide is added until the pH is 9-10. Following extraction with dichloromethane (2×200 ml), the compound is treated with ethereal hydrogen chloride. The salt is recrystallized from methanol-ethyl acetate to give 6.20 g of (+) 4,5,5a,6,7,8-hexahydro-6-propylthiazolo[4,5-f]quinolin-2-amine, dihydrochloride; mp 266°-268° C. (dec.). $[\alpha]_D = +146.5°$ (C=1.14, H$_2$O).

EXAMPLE 16a (−) 4,5,5a,6,7,8-Hexahydro-6-propylthiazolo[4,5-f]quinolin-2-amine In a process analogous to Example 16 by substituting (+)-ditoluoyl-D-tartaric acid hydrate for (−)-ditoluoyl-L-tartaric acid, the title compound can be prepared as its dihydrochloride salt; mp 267°-270° C. (dec.). $[\alpha]_D = -140.6°$ (C=1.05, H$_2$O).

EXAMPLE 16b (+) 4,5,5a,6,7,8-Hexahydro-6-methylthiazolo[4,5-f]quinolin-2-amine In a process analogous to Example 16 by substituting (±) N-(4,5,5a,6,7,8-hexahydro-6-methylthiazolo[4,5-f]quinolin-2-yl)-2-methylpropanamide (Example 15) for (±) N-(4,5,5a,6,7,8-hexahydro-6-propylthiazolo[4,5-f]quinolin-2-yl)-2-methylpropanamide (Example 15c), the title compound can be prepared as its dihydrochloride salt, hydrate; mp 265°-267° C. (dec.). $[\alpha]_D = +164.4°$ (C=1.17, H$_2$O).

EXAMPLE 16c (−) 4,5,5a,6,7,8-Hexahydro-6-methylthiazolo[4,5-f]quinolin-2-amine In a process analogous to Example 16b, by substituting (+)-ditoluoyl-D-tartaric acid hydrate for (−)-ditoluoyl-L-tartaric acid, the title compound can be prepared as its dihydrochloride salt, hydrate; mp 264°-266° C. (dec.). $[\alpha]_D = -145.5°$ (C=1.16, H$_2$O).

EXAMPLE 17

(±) trans-4,5,5a,6,7,8,9,9a-Octahydro-6-propylthiazolo[5,4-f]quinolin-2-amine

An intimate mixture is formed between 12.0 g of (±) trans-octahydro-1-propyl-6(2H)-quinolinone (U.S. Pat. No. 4,198,415) and 11.4 g of thiourea. To this mixture is added 18.24 g of iodine, while stirring the thick paste with a glass rod. The mixture is heated at 130° C. for 3 hours. The resulting dark mixture is dissolved in 250 ml boiling water, gravity-filtered and cooled to room temperaure. The solution is made basic with concentrated ammonium hydroxide and extracted with ethyl acetate. The organic phase is dried over magnesium sulfate and evaporated in-vacuo. The resulting residue is purified by medium-pressure liquid chromatography (silica gel; 1% methanol, 1% ammonium hydroxide, 98% ethyl acetate) to obtain 5.0 g of (±) trans-4,5,5a,6,7,8,9,9a-octahydro-6-propylthiazolo[5,4-f]quinolin-2-amine and 6.0 g of (±) trans-4,4a,5,6,7,8,8a,9-octahydro-5-n-propylthiazolo[4,5-g]quinolin-2-amine (U.S. Pat. No. 4,537,893). The former compound is dissolved in diethyl ether and treated with gaseous hydrogen chloride to give a gummy precipitate. The salt is refluxed with 50 ml methanol for several minutes. After cooling to 0° C., the crystalline salt is filtered. The yellow solid is characterized as the dihydrochloride of the title compound, containing 0.25 molecules of water; mp 281°–282° C.

EXAMPLE 18

(±) 4,5,5a,6,7,8-Hexahydro-6-propylthiazolo[5,4-f]quinolin-2-amine

A solution of 7,8-dihydro-6(5H)-quinolinone 10.0 g (68 mmol) (*Journal of Organic Chemistry*, Vol. 36, pp. 279–284, (1971)), in 100 ml 48% hydrobromic acid is cooled in an ice-water bath and treated dropwise with bromine, 10.9 g (68 mmol). The mixture is stirred at 0° C. for 15 minutes and the solvent is removed in-vacuo. The residue is dissolved in 100 ml methanol and refluxed with thiourea, 5.32 g (70 mmol), for 15 hours. The solvent is evaporated in-vacuo and the residue is recrystallized from ethanol to yield 4,5-dihydro-thiazolo[5,4-f]-quinolin-2-amine, hydrobromide.

The free base of 4,5-dihydrothiazolo[5,4-f]quinolin-2-amine, 5.0 g (20 mmol), is refluxed in 250 ml ethanol with 6.8 g (40 mmol) of 1-iodopropane for 20 hours. The solvent is removed in-vacuo and the 2-amino-4,5-dihydrothiazolo[5,4-f]quinolinium iodide which remains is dissolved in 200 ml methanol and treated with 1.7 g (50 mmol) of sodium borohydride in small portions, at 0° C. After 1 hour, 50 ml of 10% hydrochloric acid is added dropwise and the volatile components are removed in-vacuo. The residue is made basic with ammonium hydroxide and extracted with ethyl acetate. The organic layer is dried over magnesium sulfate, evaporated and the residue is chromatographed to yield (±)-4,5,5a,6,7,8-hexahydro-6-propylthiazolo-[5,4-f]quinolin-2-amine.

EXAMPLE 19

(±) cis and trans-2-Amino-6,6a,8,9,10,10a-hexahydropyrido[2,3-h]quinazoline-7(5H)-carboxylic acid, 1,1-dimethylethyl ester To a refluxing solution, under nitrogen, of 8.89 g (35 mmol) of cis and trans octahydro-5-oxo-1(2H)-quinolinecarboxylic acid, 1,1-dimethylethyl ester, (Example 8), in 400 ml of toluene is added dropwise a solution of 6.37 g (43.8 mmol) of tris-(dimethylamino)methane in 200 ml of toluene. The solution is refluxed for 2 hours. The reaction mixture is concentrated and the residue is dissolved in 500 ml of methanol. To the methanol solution is added 12.64 g (70.1 mmol) of guanidine carbonate, and the reaction mixture is refluxed, under nitrogen, for 12 hours. The mixture is concentrated and partitioned between brine and chloroform. The organic phase is separated, dried over magnesium sulfate, filtered and concentrated to a yellow solid. Medium pressure chromatography (silica gel, ethyl acetate) afforded 4.55 g (51%) of recovered starting ketone, 0.94 g (8.8%) of (±) cis-2-amino-6,6a,8,9,10,10a-hexahydropyrido[2,3-h]quinazoline-7(5H)-carboxylic acid, 1,1-dimethylethyl ester ($R_f$=0.33 (ethyl acetate)) as a foamy off-white solid, mp 178°–182° C., and 2.47 g (23%) of (±) trans-2-amino-6,6a,8,9,10,10a-hexahydropyrido[2,3-h]quinazoline-7(5H)-carboxylic acid, 1,1-dimethylethyl ester ($R_f$=0.27 (ethyl acetate)) as a white solid, mp 200°–206° C. (dec.).

EXAMPLE 20

(±) trans-(5,6,6a,7,8,9,10,10a-Octahydropyrido[2,3-h]quinazolin-2-yl)-carbamic acid, phenylmethyl ester To a solution of 0.21 g (7.26 mmol) of (±) trans-2-amino-6,6a,8,9,10,10a-hexahydropyrido [2,3-h]quinazoline-7(5H)-carboxylic acid, 1,1-dimethylethyl ester, (Example 19), in 200 ml of a mixture of tetrahydrofuran and saturated potassium carbonate (1:1) is added dropwise with stirring a solution of 1.6 ml (11.21 mmol) of benzyl chloroformate in 50 ml of tetrahydrofuran. The mixture is stirred at room temperature, under nitrogen, for 12 hours, the layers are separated and the aqueous phase is washed with ethyl acetate (2× 100 ml). The combined organic extract is dried over magnesium sulfate, filtered and concentrated to give 4.13 g of the crude carbobenzyloxy protected amino-pyrimidine as a light yellow oil.

A solution of the previous carbobenzyloxy protected amino-pyrimidine and 20 ml of trifluoroacetic acid in 200 ml of chloroform is stirred at room temperature, under nitrogen, for 48 hours. The mixture is concentrated to dryness, and then partitioned between chloroform and saturated potassium carbonate. The chloroform extract is dried over magnesium sulfate, filtered and concentrated to an oily solid. The oily solid is washed with diethyl ether and vacuum dried affording 1.88 g (76%) of the title compound as a light tan broad-melting solid; mp 155°–195° C. (dec.).

EXAMPLE 21

(±) trans-(5,6,6a,7,8,9,10,10a-Octahydro-7-propyl-pyrido[2,3-h]quinazolin-2-yl)-carbamic acid, phenylmethyl ester A mixture of 1.74 g (5.14 mmol) of (±) trans-(5,6,6a,7,8,9,10,10a-octahydropyrido[2,3-h]quinazolin-2-yl)-carbamic acid, phenylmethyl ester, (Example 20), 3.6 g (26.05 mmol) of finely ground potassium carbonate and 2.5 ml (25.63 mmol) of 1-iodopropane in 250 ml acetonitrile is refluxed, under nitrogen, for 24 hours. The suspension is cooled, filtered through a pad of Celite, concentrated and partitioned between brine and chloroform. The chloroform extract is separated, dried over magnesium sulfate, filtered and concentrated to a viscous brown oil. Medium pressure chromatography (silica gel, 2% ammonium hydroxide-98% ethyl acetate) afforded 1.41 g (72%) of the title compound as a white solid; mp 174°–177° C.

EXAMPLE 22

(±) trans-5,6,6a,7,8,9,10,10a-Octahydro-7-propyl-pyrido[2,3-h]quinazolin-2-amine, dihydrochloride A mixture of 0.62 g (1.63 mmol) of (±) trans-(5,6,6a,7,8,9,10,10a-octahydro-7-propylpyrido[2,3-h]quinazolin-2-yl)-carbamic acid, phenylmethyl ester, (Example 21), in 50 ml of methanol containing 0.15 g of 20% Pd/C is stirred, under a hydrogen atmosphere, for 4 hours. The mixture is filtered and concentrated to 0.49 g of an off-white solid. The dihydrochloride salt is prepared and recrystallized from methanol/diethyl ether affording 0.23 g (44%) of the title compound as a light brown solid containing one-quarter of a mole of water; mp 211°–214° C. (dec.).

EXAMPLE 23

5,6-Dihydropyrido[2,3-h]quinazolin-2-amine

To a refluxing solution, under nitrogen, of 45.0 g (0.306 mol) of 7,8-dihydro-5(6H)-quinolinone, (Example 1), in 750 ml of toluene is added dropwise a solution of 49.8 g (0.343 mol) of tris(dimethylamino)-methane in 250 ml of toluene. The solution is refluxed for 2 hours, cooled and concentrated. The residue is dissolved in 1 l of methanol and treated with 66.2 g (0.367 mol) of guanidine carbonate. The reaction mixture is refluxed, under nitrogen, for 2 hours. The mixture is concentrated to a green solid, the solid is washed with 500 ml of water, filtered and vacuum dried to give 69.1 g of crude product. Recrystallization from acetonitrile affords 6.8 g (77%) of the title compound as a light brown solid; mp 220°–226° C.

EXAMPLE 24

(±) 5,6,6a,7,8,9-Hexahydro-7-methylpyrido[2,3-h]quinazolin-2-amine

A suspension of 5.00 g (25.2 mmol) of 5,6-dihydropyrido[2,3-h]quinazolin-2-amine, (Example 23), in 300 ml of acetonitrile is refluxed, under nitrogen, for 2 hours, and then gravity filtered. Iodomethane, 16.0 ml (257 mmol), is added to the filtrate and the solution is refluxed, under nitrogen, for 12 hours. The mixture is cooled and filtered. The solid is washed with diethyl ether and vacuum dried to give 3.28 g (38.2%) of 2-amino-5,6-dihydro-7-methylpyrido [2,3-h]quinazolinium iodide as a yellow-orange solid; mp 237°–240° C. (dec.).

To a solution of 1.78 g (47.0 mmol) of sodium borohydride in 100 ml of methanol, containing 10 ml of 6N sodium hydroxide, is added dropwise with stirring a solution of 3.20 g (9.41 mmol) of 2-amino-5,6-dihydro-7-methylpyrido[2,3-h]quinazolinium iodide, in 200 ml of a mixture of methanol and water (1:1). The solution is stirred at room temperature for 2 hours, cooled, acidified by dropwise addition of 10% hydrochloric acid and stirred at room temperature for 2 hours. The solution is concentrated, basified with concentrated ammonium hydroxide and extracted with chloroform. The chloroform extract is dried over magnesium sulfate, filtered and concentrated to a brown oil. Medium pressure chromatography (silica gel, 2% ammonium hydroxide—2% methanol—96% ethyl acetate) affords 0.45 g (22.2%) of the title compound as an orange solid; mp 204°–213° C.

EXAMPLE 24a (±) 5,6,6a,7,8,9-Hexahydro-7-propylpyrido[2,3-h]quinazolin-2-amine In a process analogous to Example 24 by substituting 1-iodopropane for iodomethane, the title compound can be prepared in acceptable yield.

EXAMPLE 24b (±) 5,6,6a,7,8,9-Hexahydro-7-(2-propenyl)-pyrido[2,3-h]quinazolin-2-amine In a process analogous to Example 24 by substituting allyl bromide for iodomethane, the title Compound can be prepared in acceptable yield.

EXAMPLE 25

(±) 5,6,6a,7,8,9-Hexahydro-7-propylpyrido[3,2-f quinazolin-3-amine

A solution of 7,8-dihydro-6(5H)-quinolinone, 10.0 g (68 mmol), (Journal of Organic Chemistry, Vol. 36, pp. 279–284, (1971)), in 100 ml toluene is heated at 100° C., under nitrogen. A solution of tris(dimethylamino)methane, 14.50 g (100 mmol), in 50 ml of toluene is added dropwise over a 15 minute period. The solution is refluxed overnight. The volatiles are removed in-vacuo and the residue is dissolved in 100 ml of methanol. Guanidine carbonate, 16.94 g (140 mmol), is added and the mixture is refluxed for 20 hours. The methanol is removed in-vacuo and the residue is partitioned between chloroform and 1% ammonium hydroxide. After drying, the organic extract is concentrated to give 9,10-dihydropyrido[3,2-f]quinazolin-2-amine. A solution of 5.0 g (25.2 mmol) of 9,10-dihydropyrido [3,2-f]quinazolin-2-amine in 250 ml of acetonitrile is treated with 5.0 ml (50 mmol) of 1-iodopropane and refluxed for 24 hours. Evaporation of the solvent leaves a solid, which is washed with diethyl ether and dried. A solution of 4.0 g (10.8 mmol) of this solid in 100 ml of methanol is added dropwise to a stirred suspension of sodium borohydride, 0.68 g (20 mmol), in 100 ml of methanol, at room temperature. After 1 hour at room temperature, 10% hydrochloric acid is carefully introduced into the reaction until pH 1–2. Stirring is continued for 1 hour, the solvent is evaporated and the residue is partitioned between chloroform and 1% ammonium hydroxide. The organic layer is dried (magnesium sulfate) and concentrated. The crude reaction mixture is then purified by chromatography to yield. (±) 5,6,6a,7,8,9-hexahydro-7-propylpyrido[3,2-f]quinazolin-3-amine.

EXAMPLE 26

(±) trans-5,6,6a,7,8,9,10,10a-Octahydro-7-propylpyrido [3,2-f]quinazolin-3-amine A solution of tris(dimethylamino)methane, 25.0 g (172 mmol), in 100 ml toluene is added dropwise, under nitrogen, to a solution of the monoethylene ketal of 1,4-cyclohexanedione, 25.0 g (160 mmol), in 300 ml of toluene. The resulting solution is evaporated in-vacuo and the residue is dissolved in 600 ml of methanol along with 38.72 g (320 mmol) of guanidine carbonate. The pH of the solution is adjusted to 9 with 15% hydrochloric acid and the mixture is refluxed for 16 hours. The solvent is evaporated and the yellow residue is washed with cold water and recrystallized from absolute ethanol to yield 11.0 g of 5,6,7,8-tetrahydro-6-ketoquinazolin-2-amine, ethylene ketal as yellow prisms; mp 214°–217° C.

A solution of 7.0 g (34 mmol) of the previous intermediate in 50 ml of trifluoroacetic acid is heated at reflux for 2 hours. The mixture is concentrated in-vacuo to a volume of about 10 ml. The mixture is then treated with acrylamide, 7.1 g (100 mmol), and heated on a steam bath overnight. The mixture is diluted with 1% ammonium hydroxide and extracted with several portions of chloroform. The organic extract is dried (magnesium sulfate) and concentrated. The residue is dissolved in 20 ml of trifluoroacetic acid and treated with 8.12 g (70 mmole) of triethylsilane, at room temperature for 5 hours. The mixture is diluted with 200 ml of chloroform and 200 ml of 5% ammonium hydroxide. The organic layer is washed with brine, dried (magnesium sulfate) and evaporated. The residue is dissolved in 200 ml of anhydrous tetrahydrofuran and treated with 70 ml of a 1 M diborane tetrahydrofuran solution. The solution is stirred at room temperature overnight, and evaporated in-vacuo. The residue is partitioned between dichloromethane and 0.1 N sodium hydroxide (200 ml of each). The organic layer is dried (magnesium sulfate) and concentrated. The residue is dissolved in 200 ml of absolute ethanol, treated with 11.9 g (70 mmole) of 1-iodopropane and 15 g of anhydrous sodium bicarbonate and the mixture is refluxed for 12 hours. After cooling, the reaction mixture is filtered through Celite and concentrated. The residue is purified by medium pressure liquid chromatography to yield (±)-trans-5,6,6a,7,8,9,10,10a-octahydro-7-propylpyrido[3,2-f]quinazolin-3-amine.

EXAMPLE 27

4,5-Dihydrooxazolo[5,4-f]quinolin-2-amine and

EXAMPLE 28

4,5-Dihydrooxazolo[4,5-f]quinolin-2-amine

A solution of 6-bromo-7,8-dihydro-5(6H- quinolinone, hydrobromide, 10.0 g (32.5 mmol), (Example 2), in 150 ml of hot water is refluxed with 6.0 g (100 mmol) of urea for 24 hours. After cooling, the solution is made basic with concentrated ammonium hydroxide and extracted with 2×250 ml of dichloromethane. The organic extract is concentrated and the residue is chromatographed (1% ammonium hydroxide, 99% ethyl acetate) to separate the two products, 4,5-dihydrooxazolo[4,5-f]quinolin-2-amine (Example 28) and 4,5-dihydrooxazolo[5,4-f]quinolin-2-amine (Example 27).

EXAMPLE 29

(±) 4,5,5a,6,7,8-Hexahydro-6-propyloxazolo[5,4-f quinolin-2-amine

A solution of 4,5-dihydrooxazolo[5,4-f]quinolin-2-amine, 5.0 g (26.7 mmol), (Example 27), in 200 ml of acetonitrile is refluxed with 1-iodopropane, 10.2 g (60 mmol), for 24 hours. The volatiles are then removed in-vacuo and the resulting solid is washed with diethyl ether and dried. The resulting 2-amino-4,5-dihydrooxazolo[5,4-f]quinolinium iodide is dissolved in 150 ml of water and treated with sodium borohydride, 1.7 g (50 mmol), in small portions. The mixture is stirred at room temperature for 2 hours. Following acidification with 10% hydrochloric acid, the mixture is stirred for another hour. The volatile components are removed in-vacuo and the residue is partitioned between chloroform and 1% ammonium hydroxide. The organic extract is concentrated and purified by column chromatography to give (±) 4,5,5a,6,7,8-hexahydro-6-propyloxazolo [5,4-f]quinolin-2-amine.

EXAMPLE 29a (±) 4,5,5a,6,7,8-Hexahydro-6-propyloxazolo[4,5-f]quinolin-2-amine In a process analogous to Example 29 by substituting 4,5-dihydrooxazolo[4,5-f]quinolin-2-amine (Example 28) for 4,5-dihydrooxazolo[5,4-f]quinolin-2-amine, the title compound can be prepared.

EXAMPLE 30

(±) trans-4,5,5a,6,7,8,9,9a-Octahydro-6-propyloxazolo [4,5-f]quinolin-2-amine and

EXAMPLE 31

(±) trans-4,5,5a,6,7,8,9,9a-Octahydro-6-propyloxazolo [5,4-f]quinolin-2-amine

A solution of 3.30 g (43.3 mmol) of the trans-6-bromooctahydro-5-oxo-1(2H)-quinolinecarboxylic acid, 1,1-dimethylethyl ester, obtained as an intermediate in Example 12, in 400 ml methanol is refluxed, under nitrogen, for 12 hours with 3.0 g (50 mmole) of urea. The solution is concentrated, basified with saturated sodium bicarbonate solution and extracted with chloroform. The organic extract is concentrated and the residue chromatographed on silica gel with dichloromethane to obtain pure trans-2-amino-4,5,5a,6,7,8,9,9a-octahydrooxazolo[4,5-f]quinoline-6-carboxylic acid, 1,1-dimethylethyl ester and trans-2-amino-4,5,5a,6,7,8,9,9a-octahydrooxazolo [5,4-f]quinoline-6-carboxylic acid, 1,1-dimethylethyl ester.

A solution of 1.5 g of either one of these intermediates in 10 ml of trifluoroacetic acid is heated at 40° C. for 2 hours, followed by concentration in-vacuo and partitioning between chloroform and dilute ammonium hydroxide solution. The organic extract is then evaporated to give either (±) trans-4,5,5a,6,7,8,9,9a-octahydrooxazolo[4,5-f]quinolin-2-amine or (±) trans-4,5,5a,6,7,8,9-9a-octahydrooxazolo [5,4-f]quinolin-2-amine, respectively.

A mixture of (±) trans-4,5,5a,6,7,8,9,9a-octahydrooxazolo[4,5-f]quinolin-2-amine, 1.46 g (5.0 mmol), 3.6 g (26 mmol) of finely ground potassium carbonate and 2.5 ml (25.6 mmol) of 1-iodopropane in 250 ml of acetonitrile is refluxed, under nitrogen, for 24 hours. The mixture is cooled, filtered through a pad of Celite, concentrated and partitioned between brine and chloroform. The organic extract is dried and concentrated. Chromatography of the mixture on silica gel gives (±) trans-4,5,5a,6,7,8,9,9a-octahydro-6-propyloxazolo[4,5-f]quinolin-2-amine. The procedure just described can be applied to (±) trans-4,5,5a,6,7,8,9,9a-octahydrooxazolo[5,4-f]quinolin-2-amine to give (±) trans-4,5,5a,6,7,8,9,9a-octahydro-6-propyloxazolo [5,4-f]quinolin-2-amine.

EXAMPLE 32

4,5-Dihydro-1H(and 2H)pyrazolo[3,4-f]quinoline

Following the procedure of Ramalingam, K., et al. (*Journal of Medicinal Chemistry*, Vol. 20, pp. 664–669 (1977)), from 33.5 g (0.228 mol) of 7,8-dihydro-5(6H)-quinolinone (Example 1) is obtained 25.0 g (64%) of the title compound after recrystallization from acetonitrile; mp 206°–211° C.

EXAMPLE 33

4,5-Dihydro-6-methyl-1H(and 2H)pyrazolo[3,4-f]quinolinium iodide

To a refluxing solution, under nitrogen, of 4.00 g (23.3 mmol) of 4,5-dihydro-1H(and 2H)pyrazolo [3,4-f]quinoline, (Example 32), in 250 ml of acetonitrile is added dropwise 14.5 ml (232.9 mmol) of iodomethane. The solution is refluxed for 12 hours, during which time a yellow solid forms. The mixture is cooled and filtered. The bright yellow solid is washed with acetonitrile and vacuum dried to give 5.33 g (73%) of the title compound; mp 228°-232° C.

EXAMPLE 34

(±) 4,5,5a,6,7,8-Hexahydro-6-methyl-1H(and 2H) pyrazolo[3,4-f]quinoline, dihydrochloride To a suspension of 3.08 g (81.4 mmol) of sodium borohydride in 100 ml of methanol, containing 10 ml of 6N sodium hydroxide, is added dropwise with stirring a solution of 5.10 g (16.3 mmol) of 4,5-dihydro-6-methyl-1H(and 2H)pyrazolo[3,4-f]-quinolinium iodide, (Example 33), in 200 ml of a mixture of methanol and water (1:1). The mixture is stirred at room temperature for 2 hours, cooled to 0° C., carefully acidified with 10% hydrochloric acid to a pH of 1-2 and stirred for 2 hours. The solution is concentrated (to remove the methanol), cooled to 0° C., basified with concentrated ammonium hydroxide to a pH of 10-11 and extracted with chloroform (2×250 ml). The combined chloroform extract is dried over magnesium sulfate, filtered and concentrated to a foamy brown solid. Medium pressure chromatography (silica gel, 2% ammonium hydroxide—98% ethyl acetate) of the crude solid affords 2.9 g (94%) of the title compound as a light yellow oil. The product is converted to 3.71 g (87%) of the dihydrochloride salt, containing one-quarter mole of water, as a yellow solid; mp 261°-265° C. (dec.).

EXAMPLE 35

4,5-Dihydro-6-propyl-1H(and 2H)pyrazolo[3,4-f]quinolinium iodide

To a refluxing solution of 4.00 g (23.3 mmol) of 4,5-dihydro-1H(and 2H)pyrazolo[3,4-f]quinoline, (Example 32), in 250 ml of acetonitrile is added dropwise 23.0 ml (235.8 mmol) of 1-iodopropane. The solution is refluxed for 12 hours, during which time the color changes to bright yellow, but no solid forms. The solution is concentrated to a foamy yellow solid. The solid is washed with diethyl ether and vacuum dried, affording 7.20 g (90%) of the title compound as an orange-yellow hygroscopic solid.

EXAMPLE 36

(±) 4,5,5a,6,7,8-Hexahydro-6-propyl-1H(and 2H) pyrazolo[3,4-f]quinoline, dihydrochloride In a process analogous to Example 34 from 7.0 g (20.52 mmole) of 4,5-dihydro-6-propyl-1H(and 2H)pyrazolo[3,4-f]quinolinium iodide, (Example 35), one obtains 2.51 g (42%) of the title compound after recrystallization from 95% ethanol/ethyl acetate; mp 224°-226° C. (dec.).

EXAMPLE 37

(±) 4,5,5a,6,7,8-Hexahydro-6-(2-propenyl)-1H(and 2H)pyrazolo[3,4-f]quinoline, dihydrochloride To a refluxing solution, under nitrogen, of 4.00 g (23.3 mmol) of 4,5-dihydro-1H(and 2H)pyrazolry [3,4-f]quinoline, (Example 32), in 300 ml of acetonitrile is added 20.0 ml (231.1 mmol) of allyl bromide. The solution is refluxed for 12 hours and concentrated to a brown solid. The solid is washed with diethyl ether, filtered and vacuum dried to give 8.94 g (>100%) of 4,5-dihydro-6-(2-propenyl)-1H(and 2H)pyrazolo[3,4-f]quinolinium bromide as a brown hygroscopic solid.

A solution of the above intermediate in 300 ml of methanol is added dropwise to a suspension of 4.4 g (116.3 mmol) of sodium borohydride in 100 ml of methanol, containing 10 ml of 6N sodium hydroxide, with stirring. The solution is stirred at room temperature for 2 hours, cooled to 0° C. and carefully acidified to pH of 1-2 with 10% hydrochloric acid. The solution is stirred at room temperature for 2 hours, concentrated (to remove the methanol), basified with concentrated ammonium hydroxide to a pH 10-11 and extracted with chloroform (2×500 ml). The combined chloroform extract is dried over magnesium sulfate, filtered and concentrated to 6.50 g (95%) of a brown oil. Medium pressure chromatography (silica gel, 1% methanol—1% ammonium hydroxide—98% ethyl acetate) affords 1.47 g (29%) of (±) 4,5,5a,6,7,8-hexahydro-6-(2-propenyl)-1H(and 2H)pyrazolo[3,4-f]quinoline as a yellow oil. The dihydrochloride salt is prepared and recrystallized from 95% ethanol/ethyl acetate to give the title compound, monohydrate, as a tan solid; mp 225°-235° C. (dec.).

EXAMPLE 38

(±) trans-4,5,5a,6,7,8,9,9a-Octahydro-6-propyl-1H(and 2H)pyrazolo[3,4-f]quinoline A solution of trans-octahydro-5-oxo-1(2H)-quinolinecarboxylic acid, 1,1-dimethylethyl ester, 0.0 g (39.5 mmol), (Example 8), in 100 ml of anhydrous tetrahydrofuran is treated, under nitrogen, with potassium t-butoxide, 4.48 g (40 mmol), followed by ethyl formate, 3.12 g (40 mmol), at room temperature for 30 minutes and at reflux for another 0 minutes. The mixture is treated with 1.28 g (40 mmol) of hydrazine, at reflux, for 2 hours. Following evaporation of the solvent in-vacuo, the residue is partitioned between chloroform and water. The organic phase is dried (magnesium sulfate) and evaporated. The residue is heated in 100 ml of trifluoroacetic acid for 1 hour in order to remove the t-butoxycarbonyl protecting group. After cooling, the mixture is diluted with 200 ml of dichloromethane and 200 ml of 10% ammonium hydroxide. The organic layer is washed with brine and dried (magnesium sulfate). The solvent is removed and the residue is chromatographed to give (±) 4,5,5a,6,7,8,9,9a-octahydro-1H(and 2H)pyrazolo [3,4-f]quinoline.

A solution of 5.0 g (28.2 mmol) of the previous intermediate in 100 ml of methanol, containing a small crystal of methyl orange, is treated with propionaldehyde, 1.74 g (30 mmol), and sodium cyanoborohydride, 1.77 g (30 mmol), at 0° C. Enough 15% hydrochloric acid is added dropwise to maintain a red color in the solution for 20 minutes. The mixture is stirred at room temperature for another hour. The solvent is removed in-vacuo and the residue is partitioned between 200 ml of 1% ammonium hydroxide and 200 ml of dichloromethane.

The organic extract is concentrated and the residue is purified by medium-pressure chromatography to yield (±) trans-4,5,5a,6,7,8,9,9a-octahydro-6-propyl-1H(and 2H) pyrazolo[3,4-f]quinoline.

EXAMPLE 39

(±) 4,5,5a,6,7,8-Hexahydro-6-propyl-1H(and 2H) pyrazolo[4,3-f]quinoline

A solution of 7,8-dihydro-6-(5H-quinolinone, 10.0 g (68 mmol), (Journal of Organic Chemistry, Vol. 36, pp. 279-284, (1971)), in 200 ml of anhydrous tetrahydrofuran is treated, under nitrogen, with potassium t-butoxide, 7.84 g (70 mmol), followed by the dropwise addition of ethyl formate, 5.18 g (70 mmole), at 0° C. The mixture is then stirred at room temperature overnight. Hydrazine, 2.24 g (70 mmol), is then added and the mixture is refluxed for 2 hours. The solvent is evaporated in-vacuo and the residue is chromatographed to yield 4,5-dihydro-1H(and 2H)pyrazolo[4,3-f]quinoline.

A solution of 4,5-dihydro-1H(and 2H) pyrazolo [4,3-f]quinoline, 5.0 g (29.2 mmol), in 50 ml of acetic anhydride is refluxed for 1 hour. The acetic anhydride is removed in-vacuo and the residue is washed with diethyl ether, filtered and dried. The resulting compound is dissolved in 150 ml of acetonitrile and refluxed with 1-iodopropane, 10.0 g (58.5 mmol) for 24 hours. The volatiles are removed in-vacuo and the residue is washed with diethyl ether and air-dried. The resulting quaternary salt is dissolved in 100 ml of methanol at room temperature and treated with sodium borohydride, 1.19 g (35 mmol), in small portions. The mixture is stirred for 1 hour, acidified with 10% hydrochloric acid and the volatiles are removed in-vacuo. The residue is partitioned between 100 ml of chloroform and 100 ml of 5% ammonium hydroxide. The organic phase is further washed with brine, dried (magnesium sulfate) and concentrated. Column chromatography of the residue yields the desired (±) 4,5,5a,6,7,8-hexahydro-6-propyl-1Hand 2H)pyrazolo[4,3-f]quinoline.

EXAMPLE 40

(±) 4,5,5a,6,7,8-Hexahydrothiazolo[4,5-f]quinolin-2-amine, dihydrochloride

A solution of 5.00 g (17.15 mmol) of (±) N-(4,5,5a,6,7,8-hexahydro-6-methylthiazolo[4,5-f]quinolin-2-yl)-2-methylpropanamide (Example 15) in 150 ml of chloroform containing 20.6 ml (19.25 mmol) of a 1.07 M solution of cyanogen bromide in chloroform is refluxed, under nitrogen, for 12 hours. The solution is concentrated and the resultant yellow oily solid is refluxed in 150 ml of 10% hydrochloric acid for 12 hours. The solution is cooled, basified with ammonium hydroxide and extracted into chloroform. The chloroform extract is dried (magnesium sulfate), filtered and concentrated to a brown oil. Medium pressure chromatography (silica gel, 5% methanol—2% ammonium hydroxide—93% ethyl acetate) followed by salt formation and recrystallization from methanol/diethyl ether affords the title compound as a tan solid; mp 277°-279° C. (dec.).

EXAMPLE 41

6,7,8,9-Tetrahydro-5H-cyclohepta[b]pyridin-5-one, monohydrochloride

To an ice-cold solution of 99.4 g (0.675 mol) of 2,3-cycloheptenopyridine (Aldrich Chemical Co.) in 450 ml of glacial acetic acid and 180 ml of concentrated sulfuric acid is added dropwise a solution of 96.0 g (0.960 mol) of chromium (VI) oxide in 200 ml of glacial acetic acid and 60 ml of water. After addition, the ice-bath is removed and the viscous solution is stirred at room temperature overnight. The mixture is recooled to 0° C., carefully basified by dropwise addition of ammonium hydroxide and extracted into chloroform. The chloroform extract is dried (magnesium sulfate), filtered and concentrated to a green oil. Medium pressure chromatography (silica gel, 75% hexane—25% ethyl acetate) affords 13.2 g of recovered 2,3-cyclohepteno-pyridine and 4.8 g (4.4%) of the free base of the title compound as a yellow oil. This oil can be converted to the hydrochloride salt and recrystallized from 95% ethanol/acetonitrile to give the title compound as a white solid; mp 155°-159° C.

EXAMPLE 42

5,6-Dihydro-4H-thiazolo[4',5':3,4]cyclohepta[1,2-b]pyridin-2-amine

To a warm solution of 4.61 g (28.60 mmol) of 6,7,8,9-tetrahydro-5H-cyclohepta[b]pyridin-5-one (Example 41) in 50 ml of 48% hydrobromic acid is added dropwise a solution of 5.00 g (31.28 mmol) of bromine in 10 ml of 48% hydrobromic acid. The solution is stirred at room temperature for 2 hours and then concentrated to an orange oil. Crystallization in 95% ethanol affords 6.93 g (75.5%) of 6-bromo-6,7,8,9-tetrahydro-5H-cyclohepta[b]pyridin-5-one, hydrobromide as a white solid; mp 193°-195° C.

A solution of 6.78 g (21.12 mmol) of 6-bromo-6,7,8,9-tetrahydro-5H-cyclohepta[b]pyridin-5-one, hydrobromide and 1.93 g (25.35 mmol) of thiourea in 100 ml of water is heated on a steam bath for 2 hours. The mixture is filtered hot through a pad of Celite to remove a small amount of insoluble solid. The filtrate is cooled, basified with ammonium hydroxide, and a precipitate is collected. Recrystallization from acetonitrile affords 4.26 g (92.8%) of the title compound as a tan solid; mp 220°-222° C. (dec.).

EXAMPLE 43

(±) 5,6,6a,7,8,9-Hexahyiro-7-propyl-4H-thiazolo [4',5':3,4]cyclohepta[1,2-b]pyridin-2-amine, dihydrochloride, and (±) 5,6,6a,7,8,9,10,10a-Octahydro-7-propyl-4H-thiazolo[4', 5':3,4]cyclohepta [1,2-b]pyridin-2-amine, dihydrochloride To a refluxing solution, under nitrogen, of 3.95 g (18.18 mmol) of 5,6-dihydro-4H-thiazolo [4',5':3,4]cyclohepta[1,2-b]pyridin-2-amine (Example 42) in 500 ml of acetonitrile is added dropwise 18.0 ml (184.6 mmol) of 1-iodopropane. The solution is refluxed for 72 hours, under nitrogen, then cooled and concentrated to a yellow solid. The solid is washed with diethyl ether and vacuum dried giving 8.02 g (>100%) of crude 2-amino-5,6-dihydro-7-propyl-4H-thiazolo[4',5':3,4]pyridinium iodide as a bright yellow solid, which is carried on without further purification.

To a solution of 3.9 g (103.1 mmol) of sodium borohydride in 500 ml of methanol containing 10 ml of 6N sodium hydroxide is added dropwise with stirring a solution of 7.93 g (20.48 mmol) of the above crude quaternary pyridinium iodide salt in 500 ml of a mixture of methanol and water (1:1). The solution is stirred at room temperature for 2 hours, cooled to 0° C. and carefully acidified with 10% hydrochloric acid to pH of 1. The acidic solution is stirred for 2 hours, concentrated (to remove the methanol), basified with ammonium hydroxide to pH of 10-11 and extracted into chloroform. The chloroform extract is dried (magnesium sulfate), filtered and concentrated to a red oil. Medium pressure chromatography (silica gel, 2% ammonium hydroxide—98% ethyl acetate), followed by hydrochloride salt formation and recrystallization from 95% ethanol/ethyl acetate affords 1.43 g (21%) of (±) 5,6,6a,7,8,9-hexahydro-7-propyl-4H-thiazolo[4′,5′:3,4-]cyclohepta[1,2-]pyridin-2-amine, dihydrochloride as a tan solid; mp 281°-282° C. (dec.) and 1.47 g (21%) of (±) 5,6,6a,7,8,9,10,10a-octahydro-7-propyl-4H-thiazolo [4′,5′:3,4]cyclohepta[1,2-b ]pyridin-2-omine, dihydrochloride, hemihydrate as a brown solid; mp 237°-242° C. (dec.).

We claim:

1. A compound of the formula

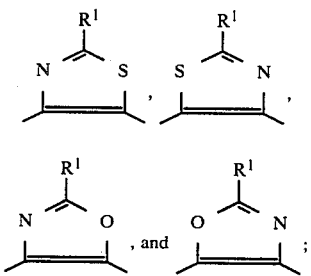

wherein --- indicates the presence of a single or double bond; HET is selected from the group consisting of

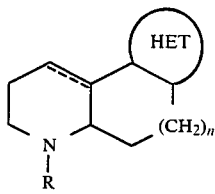

, and

R is hydrogen, alkyl, alkenyl, cycloalkylalkyl, arylalkyl,

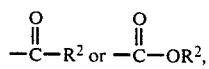

in which $R^2$ is alkyl or arylalkyl; $R^1$ is hydrogen, alkyl, or $NR^3R^4$ in which $R^3$ is hydrogen or alkyl and $R^4$ is hydrogen, alkyl, alkenyl, cycloalkylalkyl, arylalkyl,

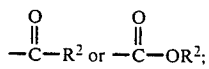

n=0, 1 or 2; and corresponding geometric and optical isomers thereof; or a pharmaceutically acceptable acid addition salt thereof.

2. A compound according to claim 1, in which R and $R^4$ are each independently hydrogen, alkyl, alkenyl, cycloalkylalkyl,

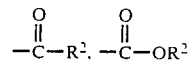

or phenylalkyl in which phenyl is substituted by one to four substituents selected from alkyl, alkoxy, halogen or trifluoromethyl or a pharmaceutically acceptable acid addition salt thereof.

3. A compound according to claim 2, wherein R is hydrogen, alkyl, alkenyl, cyclopropylmethyl,

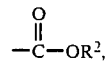

benzyl or phenylethyl and $R^1$ is hydrogen or $NR^3R^4$ in which $R^3$ is hydrogen or alkyl and $R^4$ is hydrogen, alkyl, benzyl,

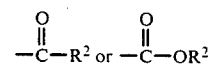

in which $R^2$ is alkyl or arylalkyl, or a pharmaceutically acceptable acid addition salt thereof.

4. A compound according to claim 3, wherein R is hydrogen, methyl, ethyl, allyl, n-propyl, n-butyl, cyclopropylmethyl,

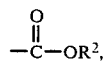

benzyl or phenylethyl and $R^1$ is hydrogen or $NR^3R^4$ in which $R^3$ is hydrogen or alkyl and $R^4$ is hydrogen, methyl, ethyl, n-propyl,

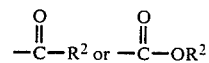

in which $R^2$ is alkyl or arylalkyl or a pharmaceutically acceptable acid addition salt thereof.

5. A compound according to claim 4, wherein R is hydrogen, methyl, ethyl, allyl, n-propyl, n-butyl, cyclopropylmethyl, benzyl or phenylethyl and $R^1$ is hydrogen or $NR^3R^4$ in which $R^3$ is hydrogen and $R^4$ is hydrogen,

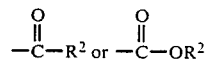

in which $R^2$ is alkyl or arylalkyl or a pharmaceutically acceptable acid addition salt thereof.

6. A compound according to claim 5, and being (±) 4,5,5a,6,7,8-hexahydro-6-propylthiazolo [4,5-f]quinolin-2-amine or a pharmaceutically acceptable acid addition salt thereof.

7. A compound according to claim 5, and being (±) trans-4,5,5a,6,7,8,9,9a-octahydrothiazolo [4,5-f]quinolin-2-amine or a pharmaceutically acceptable acid addition salt thereof.

8. A compound according to claim 5, and being (±) trans-4,5,5a,6,7,8,9,9a-octahydro-6-propylthiazolo[4,5-f]quinolin-2-amine or a pharmaceutically acceptable acid addition salt thereof.

9. A compound according to claim 5, and being (+) 4,5,5a,6,7,8-hexahydro-6-propylthiazolo [4,5-f]quinolin- 2-amine or a pharmaceutically acceptable acid addition salt thereof.

10. A compound according to claim 5, and being (−) 4,5,5a,6,7,8-hexahydro-6-propylthiazolo [4,5-f]quinolin-2-amine or a pharmaceutically acceptable acid addition salt thereof.

11. A compound according to claim 5, and being (±) 4,5,5a,6,7,8-hexahydrothiazolo[4,5-f]quinolin-2-amine or a pharmaceutically acceptable acid addition salt thereof.

12. A compound according to claim 5, and being (+) 4,5,5a,6,7,8-hexahydrothiazolo[4,5-f]quinolin-2-amine or a pharmaceutically acceptable acid addition salt thereof.

13. A compound according to claim 5, and being (−) 4,5,5a,6,7,8-hexahydrothiazolo[4,5-f]quinolin-2-amine or a pharmaceutically acceptable acid addition salt thereof.

14. A compound according to claim 5, and being (±) 4,5,5a,6,7,8-hexahydro-6-methylthiazolo [4,5-f]quinolin-2-amine or a pharmaceutically acceptable acid addition salt thereof.

15. A compound according to claim 5, and being (+) 4,5,5a,6,7,8-hexahydro-6-methylthiazolo [4,5-f]quinolin-2-amine or a pharmaceutically acceptable acid addition salt thereof.

16. A compound according to claim 5, and being (−) 4,5,5a,6,7,8-hexahydro-6-methylthiazolo [4,5-f]quinolin-2-amine or a pharmaceutically acceptable acid addition salt thereof.

17. A compound according to claim 5, and being (±) 6-ethyl-4,5,5a,6,7,8-hexahydrothiazolo [4,5-f]quinolin-2-amine or a pharmaceutically acceptable acid addition salt thereof.

18. A compound according to claim 5, and being (+) 6-ethyl-4,5,5a,6,7,8-hexahydrothiazolo [4,5-f]quinolin-2-amine or a pharmaceutically acceptable acid addition salt thereof.

19. A compound according to claim 5, and being (−) 6-ethyl-4,5,5a,6,7,8-hexahydrothiazolo [4,5-f]quinolin-2-amine or a pharmaceutically acceptable acid addition salt thereof.

20. A compound according to claim 5, and being (±) 6-butyl-4,5,5a,6,7,8-hexahydrothiazolo [4,5-f]quinolin-2-amine or a pharmaceutically acceptable acid addition salt thereof.

21. A compound according to claim 5, and being (+) 6-butyl-4,5,5a,6,7,8-hexahydrothiazolo [4,5-f]quinolin-2-amine or a pharmaceutically acceptable acid addition salt thereof.

22. A compound according to claim 5, and being (−) 6-butyl-4,5,5a,6,7,8-hexahydrothiazolo [4,5-f]quinolin-2-amine or a pharmaceutically acceptable acid addition salt thereof.

23. A compound according to claim 5, and being (±) 4,5,5a,6,7,8-hexahydro-6-(2-propenyl) thiazolo[4,5-f]quinolin-2-amine or a pharmaceutically acceptable acid addition salt thereof.

24. A compound according to claim 5, and being (+) 4,5,5a,6,7,8-hexahydro-6-(2-propenyl) thiazolo[4,5-]f-quinolin-2-amine or a pharmaceutically acceptable acid addition salt thereof.

25. A compound according to claim 5, and being (−) 4,5,5a,6,7,8-hexahydro-6-(2-propenyl) thiazolo[4,5-f]quinolin-2-amine or a pharmaceutically acceptable acid addition salt thereof.

26. A compound according to claim 5, and being (±) 6-(cyclopropylmethyl)-4,5,5a,6,7,8-hexahydrothiazolo [4,5-f]quinolin-2-amine or a pharmaceutically acceptable acid addition salt thereof.

27. A compound according to claim 5, and being (±) 4,5,5a,6,7,8-hexahydro-6-(2-phenylethyl) thiazolo[4,5-f]quinolin-2-amine or a pharmaceutically acceptable acid addition salt thereof.

28. A compound according to claim 5, and being (+) 4,5,5a,6,7,8-hexahydro-6-(2-phenylethyl) thiazolo[4,5-f]quinolin-2-amine or a pharmaceutically acceptable acid addition salt thereof.

29. A compound according to claim 5, and being (±) 4,5,5a,6,7,8-hexahydro-6-(phenylmethyl) thiazolo[4,5-f]quinolin-2-amine or a pharmaceutically acceptable acid addition salt thereof.

30. A compound according to claim 5, and being (±) N-(4,5,5a,6,7,8-hexahydro-6-methylthiazolo [4,5-f]quinolin-2-yl)-2-methylpropanamide or a pharmaceutically acceptable acid addition salt thereof.

31. A compound according to claim 5, and being (+) N-(4,5,5a,6,7,8-hexahydro-6-methylthiazolo [4,5-f]quinolin-2-yl)-2-methylpropanamide or a pharmaceutically acceptable acid addition salt thereof.

32. A compound according to claim 5, and being (−) N-(4,5,5a,6,7,8-hexahydro-6-methylthiazolo [4,5-f]quinolin-2-yl)-2-methylpropanamide or a pharmaceutically acceptable acid addition salt thereof.

33. A compound according to claim 5, and being (±) N-(4,5,5a,6,7,8-hexahydro-6-propylthiazolo [4,5-f]quinolin-2-yl)acetamide or a pharmaceutically acceptable acid addition salt thereof.

34. A compound according to claim 5, and being (±) N-(4,5,5a,6,7,8-hexahydro-6-methylthiazolo [4,5-f]quinolin-2-yl)acetamide or a pharmaceutically acceptable acid addition salt thereof.

35. A compound according to claim 5, and being (+) N-(4,5,5a,6,7,8-hexahydro-6-methylthiazolo [4,5-f]quinolin-2-yl)acetamide or a pharmaceutically acceptable acid addition salt thereof.

36. A compound according to claim 5, and being (−) N-(4,5,5a,6,7,8-hexahydro-6-methylthiazolo [4,5-f]quinolin-2-yl)acetamide or a pharmaceutically acceptable acid addition salt thereof.

37. A compound according to claim 5, and being (+) N-(4,5,5a,6,7,8-hexahydro-6-propylthiazolo [4,5-f]quinolin-2-yl)acetamide or a pharmaceutically acceptable acid addition salt thereof.

38. A compound according to claim 5, and being (−) N-(4,5,5a,6,7,8-hexahydro-6-propylthiazolo [4,5-f]quinolin-2-yl)acetamide or a pharmaceutically acceptable acid addition salt thereof.

39. A compound according to claim 5, and being (±) N-[4,5,5a,6,7,8-hexahydro-6-(2-propenyl) thiazolo[4,5-f]quinolin-2-yl]acetamide or a pharmaceutically acceptable acid addition salt thereof.

40. A compound according to claim 5, and being (+) N-[4,5,5a,6,7,8-hexahydro-6-(2-propenyl) thiazolo[4,5-f]quinolin-2-yl]acetamide or a pharmaceutically acceptable acid addition salt thereof.

41. A compound according to claim 5, and being (−) N-[4,5,5a,6,7,8-hexahydro-6-(2-propenyl) thiazolo[4,5-f]quinolin-2-yl]acetamide or a pharmaceutically acceptable acid addition salt thereof.

42. A compound according to claim 5, and being (±) N-(4,5,5a,6,7,8-hexahydro-6-propylthiazolo [4,5-f]quinolin-2-yl)-2-methylpropanamide or a pharmaceutically acceptable acid addition salt thereof.

43. A compound according to claim 5, and being (+) N-(4,5,5a,6,7,8-hexahydro-6-propylthiazolo [4,5- f]quinolin-2-yl)-2-methylpropanamide or a pharmaceutically acceptable acid addition salt thereof.

44. A compound according to claim 5, and being (−) N-(4,5,5a,6,7,8-hexahydro-6-propylthiazolo [4,5-f]quinolin-2-yl)-2-methylpropanamide or a pharmaceutically acceptable acid addition salt thereof.

45. A compound according to claim 5, and being (±) trans-4,5,5a,6,7,8,9,9a-octahydro-6-propylthiazolo[5,4-f]quinolin-2-amine or a pharmaceutically acceptable acid addition salt thereof.

46. A compound according to claim 5, and being (+) trans-4,5,5a,6,7,8,9,9a-octahydro-6-propylthiazolo[5,4-f]quinolin-2-amine or a pharmaceutically acceptable acid addition salt thereof.

47. A compound according to claim 5, and being (−) trans-4,5,5a,6,7,8,9,9a-octahydro-6-proylthioazolo[5,4-f]quinolin-2-amine or a pharmaceutically acceptable acid addition salt thereof.

48. A compound according to claim 5, and being (±) 4,5,5a,6,7,8-hexahydro-6-propylthiazolo [5,4-f]quinolin-2-amine or a pharmaceutically acceptable acid addition salt thereof.

49. A compound according to claim 5, and being (±) 4,5,5a,6,7,8-hexahydro-6-propyloxazolo [5,4-f]quinolin-2-amine or a pharmaceutically acceptable acid addition salt thereof.

50. A compound according to claim 5, and being (±) 4,5,5a,6,7,8-hexahydro-6-propyloxazolo [4,5-f]quinolin-2-amine or a pharmaceutically acceptable acid addition salt thereof.

51. A compound according to claim 5, and being (±) trans-4,5,5a,6,7,8,9,9a-octahydro-6-propyloxazolo[4,5-f]quinolin-2-amine or a pharmaceutically acceptable acid addition salt thereof.

52. A compound according to claim 5, and being (±) trans-4,5,5a,6,7,8,9,9a-octahydro-6-propyloxazolo[5,4-f]quinolin-2-amine or a pharmaceutically acceptable acid addition salt thereof.

53. A method of treating psychoses, hypertension, galactorrhea, amenorrhea, menstrual disorders, sexual dysfunction, Parkinson's disease, Huntington's chorea or depression comprising administering to a host suffering therefrom a therapeutic effective amount of a compound according to claim 1 in unit dosage form.

54. A method of treating schizophrenia comprising administering to a host suffering therefrom a therapeutic effective amount of a compound according to claim 1 in unit dosage form.

55. A pharmaceutical composition adapted for administration as a dopaminergic, antipsychotic or antihypertensive agent comprising a therapeutic effective amount of a compound according to claim 1 in admixture with a pharmaceutically acceptable excipient, diluent or carrier.

* * * * *